(12) United States Patent
Armitage

(10) Patent No.: US 10,132,780 B2
(45) Date of Patent: Nov. 20, 2018

(54) DEVICES, SYSTEMS AND METHODS OF DETECTING DEFECTS IN WORKPIECES

(71) Applicant: UNIVERSITY OF EXETER, Exeter, Devon (GB)

(72) Inventor: Peter Robert Armitage, Exeter (GB)

(73) Assignee: UNIVERSITY OF EXETER, Exeter (GB)

(*) Notice: Subject to any disclaimer, the term of this patent is extended or adjusted under 35 U.S.C. 154(b) by 862 days.

(21) Appl. No.: 14/319,342

(22) Filed: Jun. 30, 2014

(65) Prior Publication Data

US 2014/0311244 A1 Oct. 23, 2014

Related U.S. Application Data

(62) Division of application No. 12/745,983, filed as application No. PCT/GB2008/004001 on Dec. 4, 2008.

(Continued)

(30) Foreign Application Priority Data

Dec. 4, 2007 (GB) .................................. 0723622.7

(51) Int. Cl.
*G01N 29/04* (2006.01)
*G01N 29/12* (2006.01)
(Continued)

(52) U.S. Cl.
CPC ............ *G01N 29/04* (2013.01); *G01N 29/043* (2013.01); *G01N 29/12* (2013.01); *G01N 29/348* (2013.01);
(Continued)

(58) Field of Classification Search
CPC .... G01N 29/043; G01N 29/12; G01N 29/348; G01N 29/42; G01N 29/4445;
(Continued)

(56) References Cited

U.S. PATENT DOCUMENTS 4,658,649 A 4/1987 Brook
5,092,336 A * 3/1992 Fink ..................... G01N 29/341
600/443

(Continued)

FOREIGN PATENT DOCUMENTS

JP 2000121613 A 4/2000

OTHER PUBLICATIONS

S. Bae et al., "New Adaptive Grain Noise Cancellation Filtering Technique", 1998, Rev. Prog. Quan. Nondest. Eval. vol. 17 pp. 759-766.*

(Continued)

*Primary Examiner* — Regis J Betsch
(74) *Attorney, Agent, or Firm* — King & Schickli, PLLC

(57) ABSTRACT

Device and method for detecting a defect in a workpiece with a broadband transducer (10), a driving circuit connected to the transducer to operate the transducer in a actuator mode, a signal output circuit connectable to operate in a sensor mode, a control for selectively connecting the transducer to the driving circuit or signal output circuit wherein the driving circuit includes at least a pair of oscillators for generating signals of at least frequencies F1 and F2 and a summer for summing the signals to provide a driving circuit for the transducer.

17 Claims, 33 Drawing Sheets

Related U.S. Application Data

(60) Provisional application No. 61/013,130, filed on Dec. 12, 2007.

(51) Int. Cl.
*G01N 29/34* (2006.01)
*G01N 29/42* (2006.01)
*G01N 29/44* (2006.01)

(52) U.S. Cl.
CPC ......... *G01N 29/42* (2013.01); *G01N 29/4445* (2013.01); *G01N 2291/014* (2013.01); *G01N 2291/106* (2013.01); *G01N 2291/2694* (2013.01)

(58) Field of Classification Search
CPC .............. G01N 29/04; G01N 2291/014; G01N 2291/106; G01N 2291/2694
See application file for complete search history.

(56) References Cited

U.S. PATENT DOCUMENTS

| | | | |
|---|---|---|---|
| 6,202,489 B1* | 3/2001 | Beffy | G01N 29/262 73/622 |
| 2006/0169029 A1* | 8/2006 | Heyman | G01V 1/001 73/52 |
| 2007/0125174 A1* | 6/2007 | Ramaswamy | G01N 3/56 73/579 |

OTHER PUBLICATIONS

Fatemi et al., "Ultrasound-Stimulated Vibro-Acoustic Spectrography", Apr. 3, 1998, Science vol. 280 pp. 82-85.*

"Industrial Application of Ultrasound", Acoustics Committee, Shanghai Society of Physics, p. 40, published by Shanghai Science & Technology Compiling and Translating House.

* cited by examiner

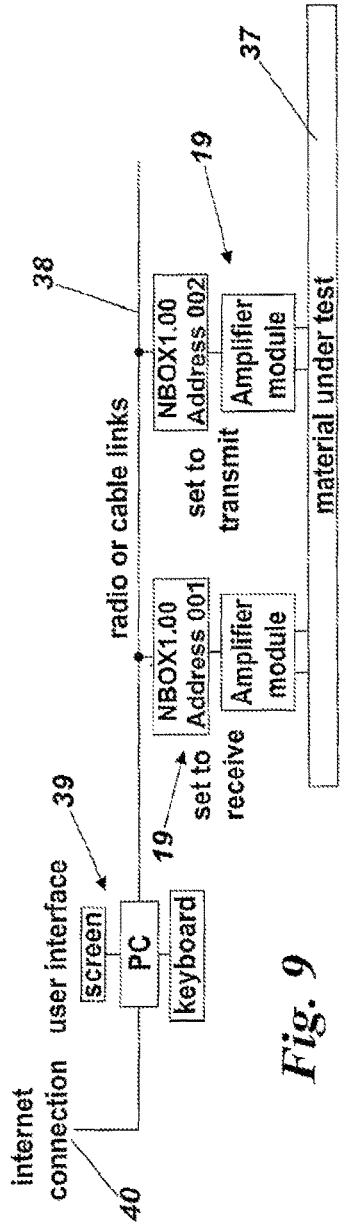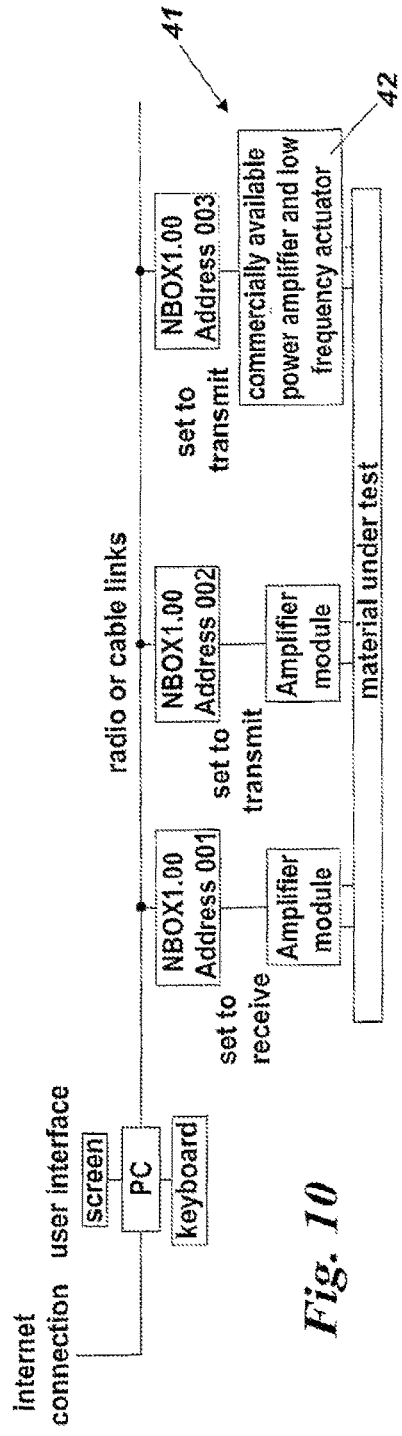
Fig. 9
Fig. 10

40KN to 46KN audio indication of structural failure
No visual damage observed sample fails at 52.5KN 40KN to 46KN audio indication of structural failure
No visual damage observed sample fails at 52.5KN 40KN to 46KN audio indication of structural failure
No visual damage observed sample fails at 52.5KN

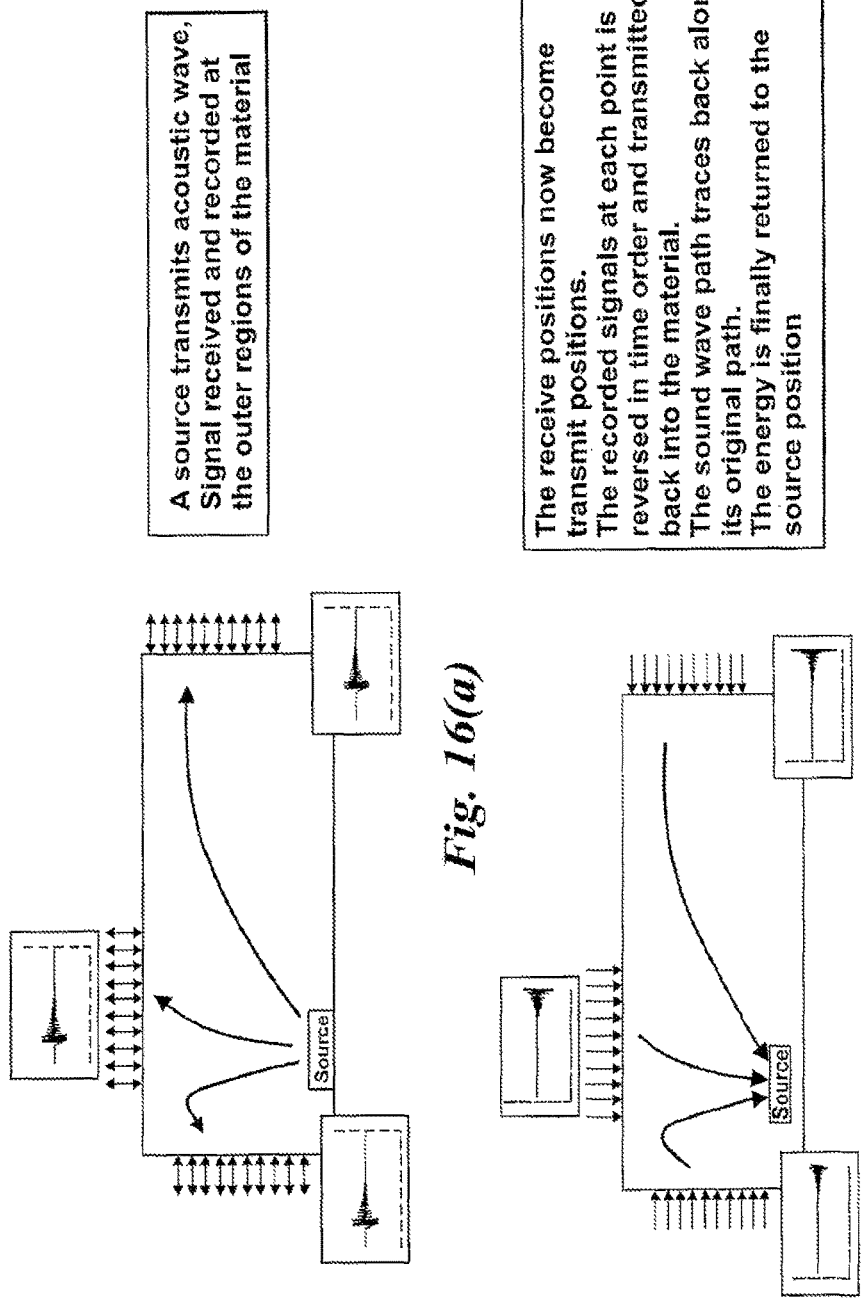

Concrete test cylinders

Cracked concrete

Undamaged concrete

The power spectra of the sum of two sine waves undamaged cube damaged cube

DEVICES, SYSTEMS AND METHODS OF DETECTING DEFECTS IN WORKPIECES

This invention relates to devices, systems and methods for use in detecting a defect in a work piece and in particular, but not exclusively, to detecting defects in parts of aircraft.

The tendency of modern design, particularly in the transport industry, is to require materials to be lighter and lighter, whilst withstanding greater stresses and strains due to such factors as increased load, faster operating speeds and more intense working timetables. For example, in their heyday the average steam engine would travel a ¼ million miles over a 20-30 year life, whilst that distance is commonly traveled in a single year at a far greater average speed by a high speed train traction unit. In the airline industry faster turn-arounds have become the key to economic operation in the low fare structure, whilst the safety requirements are ever increasing. The desire to reduce vehicle weight has led to greater use of composite materials and in particular laminated materials and many of the non-destructive testing techniques that have previously been developed for metal parts are rather inadequate for detecting defects in composite parts and the test may take significant periods to set up because of complex testing techniques.

The present invention describes a number of embodiments, which serve to mitigate one or more of these problems.

From one aspect the invention consists in the device for use in detecting a defect in a workpiece including:
(a) a broad band transducer for contacting the workpiece;
(b) a driving circuit connectable to the transducer to operate the transducer in an actuator mode;
(c) a signal output circuit connectable to operate the transducer in a sensor mode; and
(d) a control for selectively connecting the transducer to the driving circuit or the signal output circuit.

Preferably the device includes a data interface and the microprocessor may form both control and the interface. The microprocessor may be linked to at least one of an analogue to digital converter; a digital-to-analogue converter; a data memory; a wireless connection and a communication link.

The driving circuit may include a pair of oscillators for generating signals of frequency $F_1$ and $F_2$ respectively and summer for summing the signals $F_1$, $F_2$ to provide a driving signal for the transducer.

The invention may also include a defect detecting system including an array of devices as set out above in a central computer linked to the interface of each device by a communication link.

The computer may be arranged for generating control signals to be sent by the communication link to instruct the controls of the respective device to operate the associated transducer in an actuator or sensor mode. The array may be in the form of a grid for extending across a workpiece in which case the computer may operate the devices in a time reversal mode and the location of the time reverse defect generated signals may be determined by determining the location of the sensor nearest the focus of the time reverse defect generated signals.

The devices may be embedded in the workpiece.

The system may additionally include a dedicated actuator, such as a narrow band actuator.

The system may additionally include a dedicated sensor.

The system may monitor the signal received by at least one device, which is in sensor mode, for one or more harmonics, such as a third harmonic, in the output signal and may produce an output in response to that detection. In addition the system may include electronic circuitry to monitor the signal frequency and may produce an output in response to that detection.

From another aspect the invention consists in a system for detecting defects including a plurality of transducers each having an interface and a configuration device for configuring at least some of the transducers as either a sensor or an actuator, a communication link connecting the interfaces to a central computer, whereby the computer can instruct the configuration devices via the interfaces to configure their respective transducer.

From a further aspect the invention consists of a method of detecting micro-cracking or de-lamination in a workpiece including: inputting a sonic or ultrasonic impasse into the workpiece; detecting the resultant signal in the workpiece; monitoring the signal to detect the appearance of harmonics, such as the third harmonic of the impulse frequency and thereby detecting the presence of micro-cracking or de-lamination.

The method may also include monitoring the signal to detect the subsequent variation in the relative magnitude of the harmonics, such as the reduction in or disappearance of the third harmonic, and thereby detecting the imminent transition to structural failure.

In an additional aspect the invention includes a method of detecting a defect in a workpiece including inputting into the workpiece two signals at respective frequencies $F_1$ and $F_2$ to create vibrations in the workpiece, detecting a resultant output at another location on the workpiece with wideband receiver and monitoring one or more of the resultant harmonics, overtones or sidebands to determine the presence or absence of a defect.

Another aspect of the invention includes a method of detecting a defect in a workpiece including:
(a) inputting a sonic or ultrasonic signal into the workpiece;
(b) singly or successively striking the workpiece with impact of various force amplitudes;
(c) detecting the frequency of the signal in the workpiece; and monitoring the frequency shift of the detected signal as a function of signal amplitude;
wherein the step of monitoring includes feeding the detected signal through a phase lock loop including a voltage controlled oscillator VCO having the sonic input frequency as its input signal and determining the frequency shift from the VCO control voltage.

Additionally another aspect of the invention includes a method of detecting a defect in a workpiece including inputting two sonic ultrasonic impulses into a workpiece, the impulses being of equal amplitude but 180° out of phase, detecting the resultant vibrations in the workpiece to generate respective output signals, summing the output signals and monitoring the amplitude of the summed signals for determining the presence or absence of a defect.

From a still further aspect the invention consists in the broad band piezoelectric transducer including:
(a) a piezoelectric element;
(b) an acoustic matching front plate; and
(c) a tungsten particle containing epoxy resin backing block for providing acoustic attenuation over a range of operating frequencies.

The backing block may contain tungsten particles of 250, 25 and <1 micron diameters. It may additionally or alternatively include a mounting rod extending through at least part of the backing block. Preferably a mounting rod is of a semi-rigid material.

Although the invention has been defined above, it is to be understood that it includes any inventive combination of the features set out above or in the following description.

The invention may be performed in various ways and specific embodiments will now be described, by way of example, with reference to the accompanying drawings, in which:

FIGS. 9 to 12 illustrate a variety of configuration transducers devices linked to a central computer for use in different test modes;

Figures 13A, 13B, 13C:
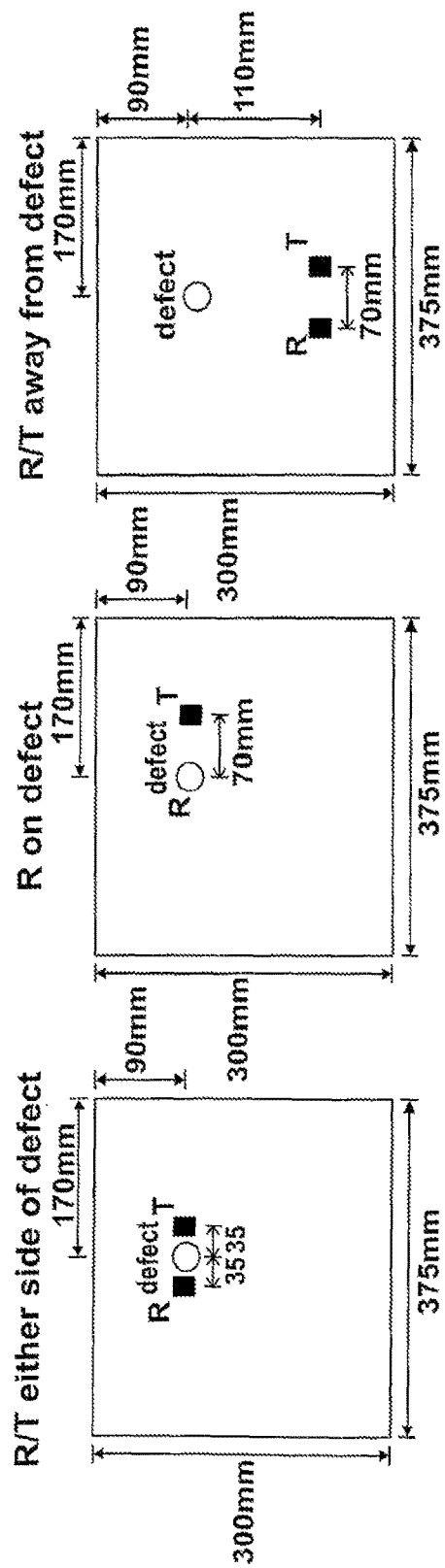
Figure 14A:
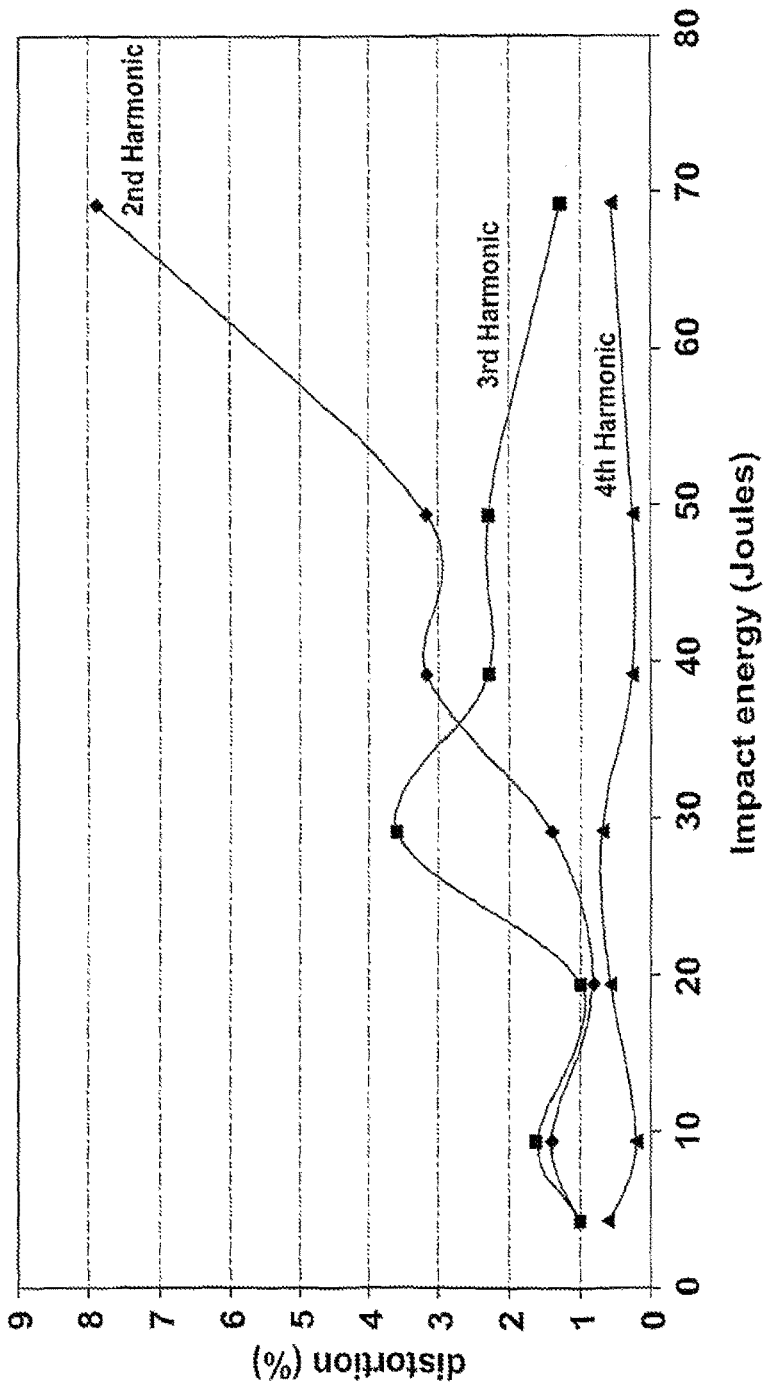
Figure 14B:
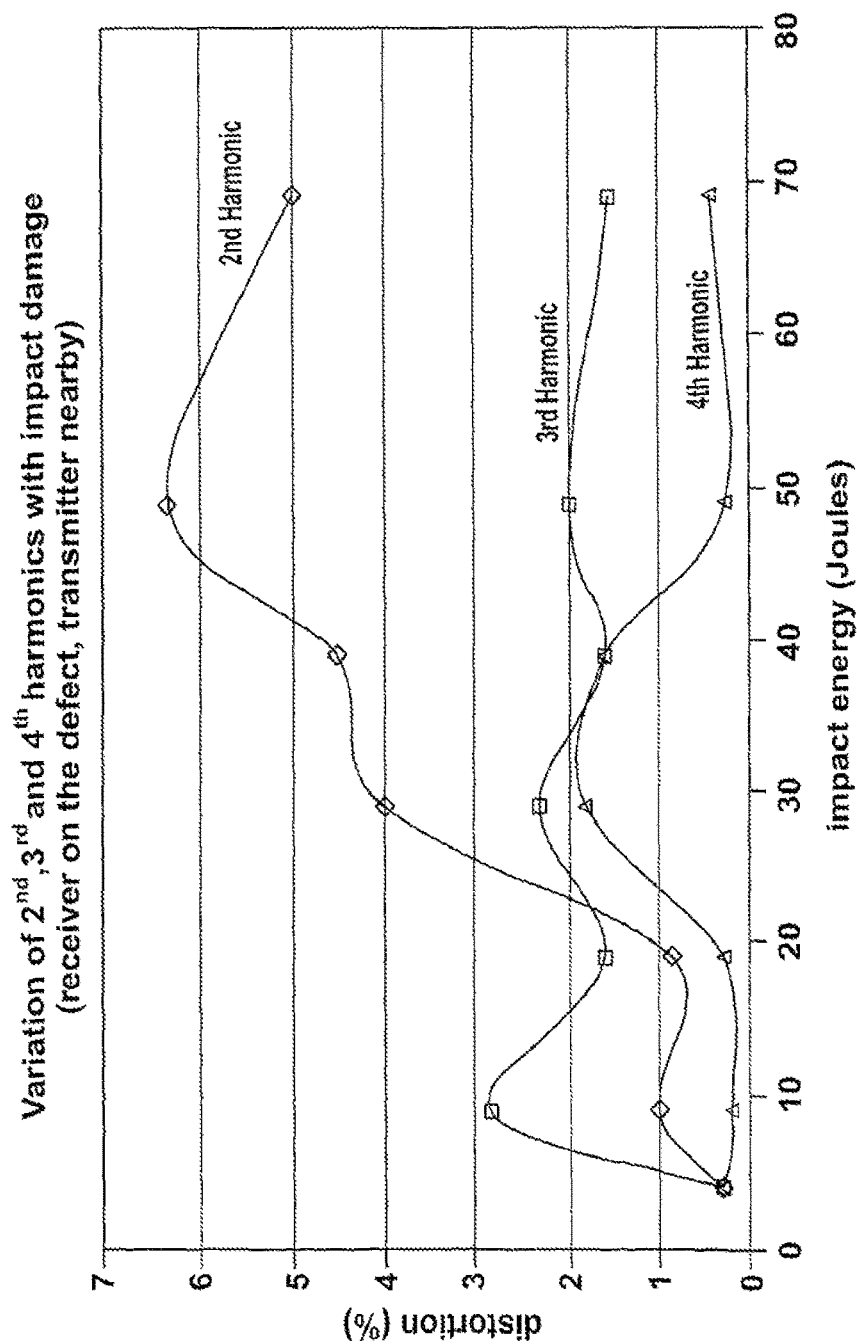
Figure 14C:
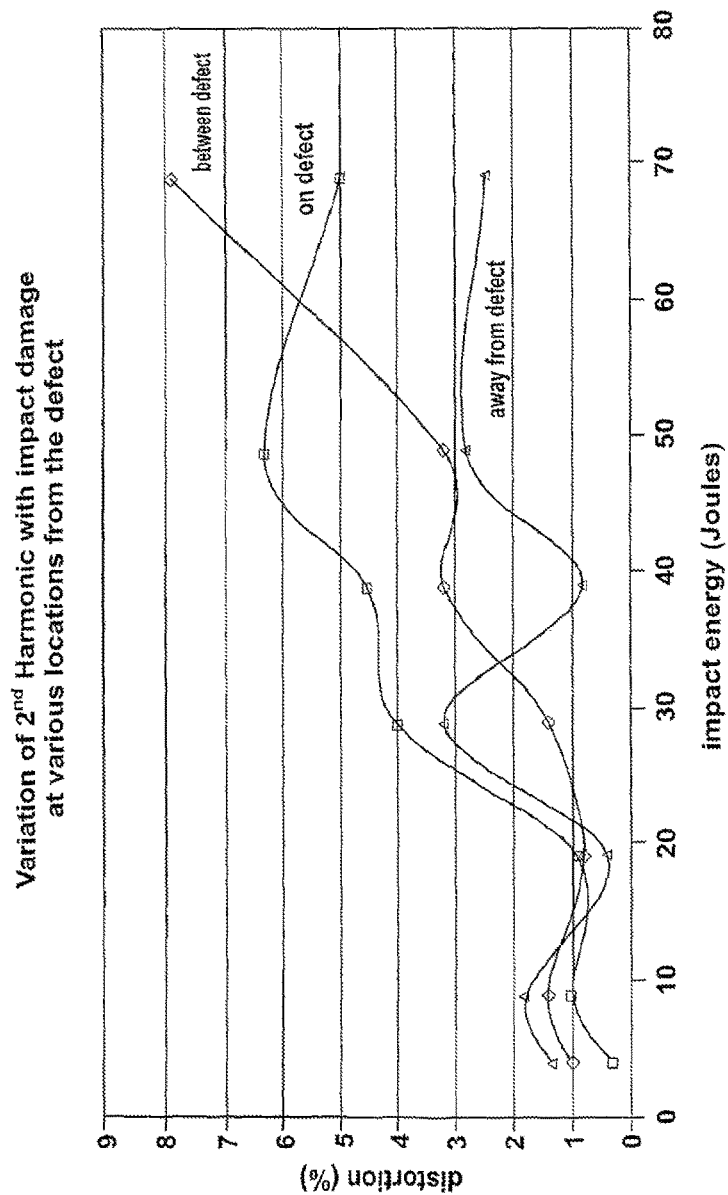
Figure 15A:
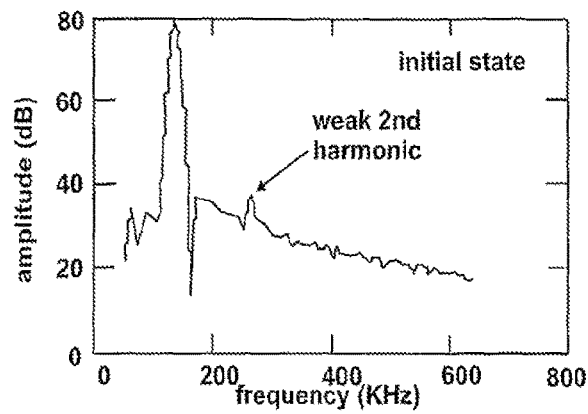
Figure 15B:
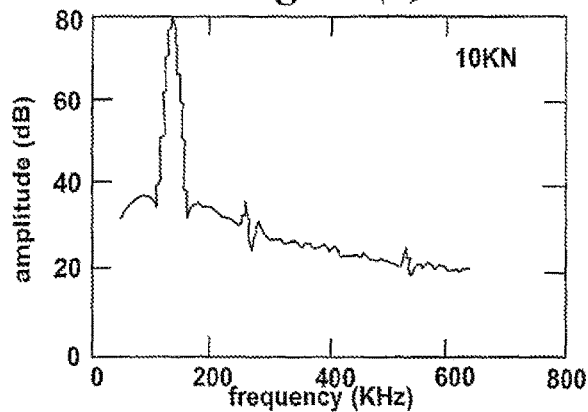
Figure 15C:
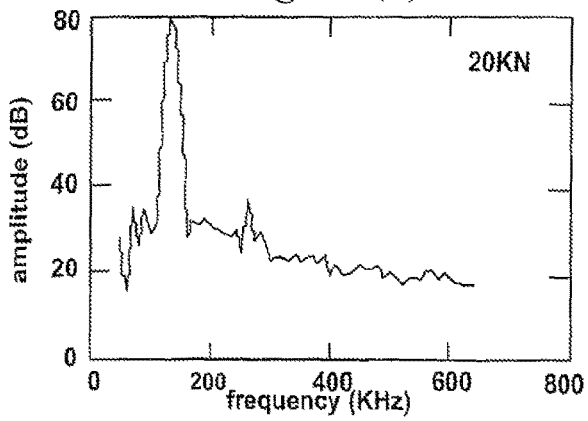
Figure 15D:
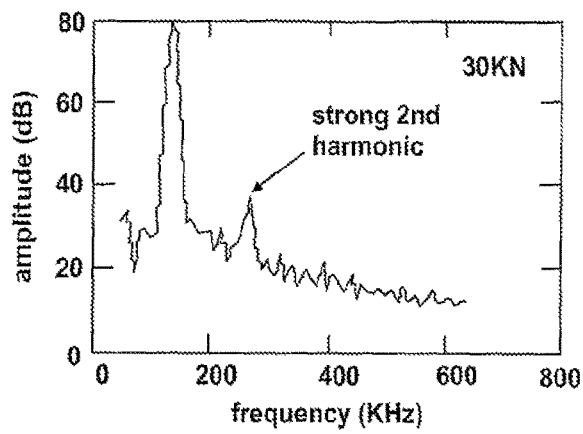
Figure 15E:
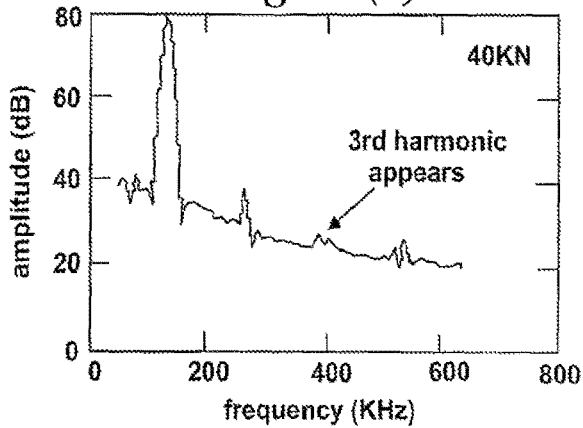
Figure 15F:
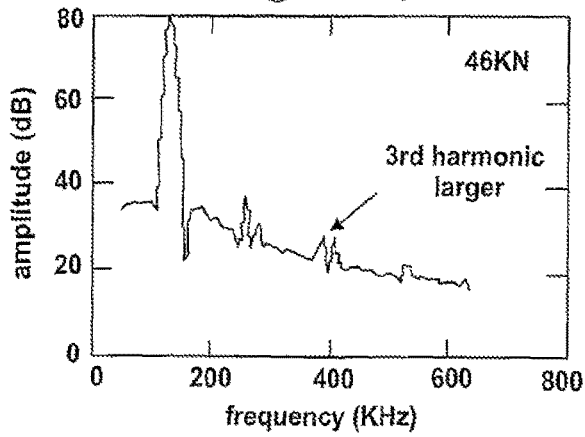
Figure 15G:
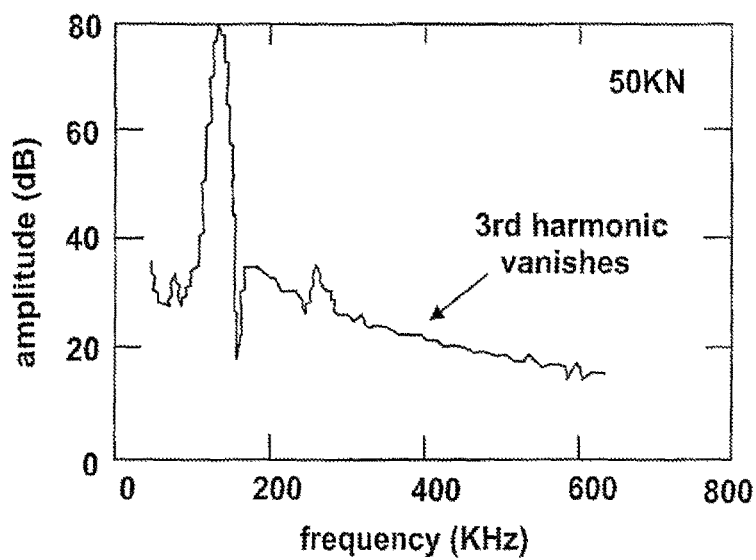
Figure 16C:
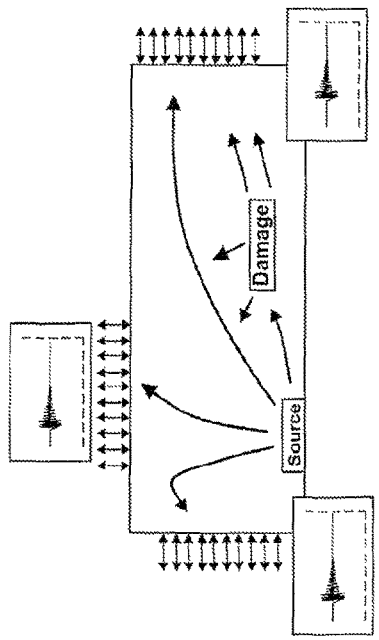
Figure 16D:
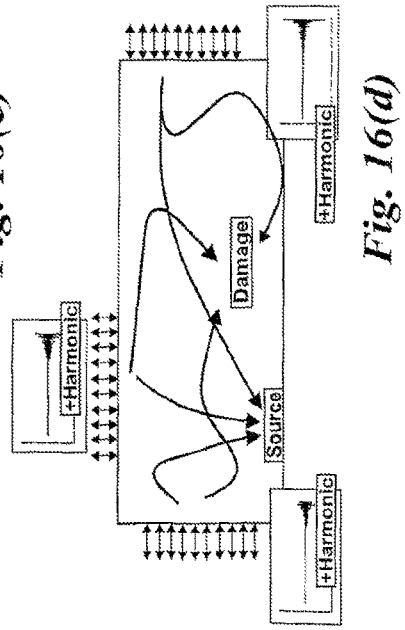
Figure 17A:
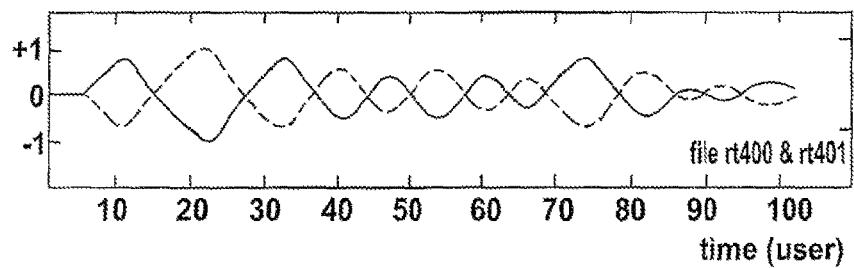
Figure 17B:
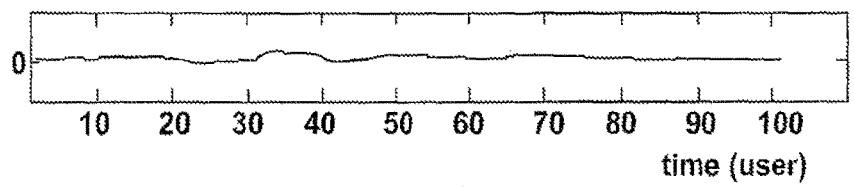
Figure 17C:
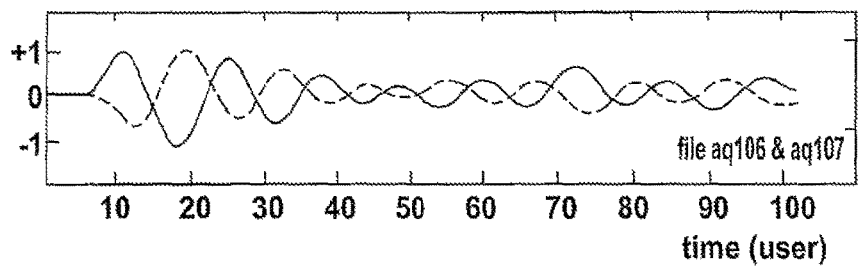
Figure 17D:
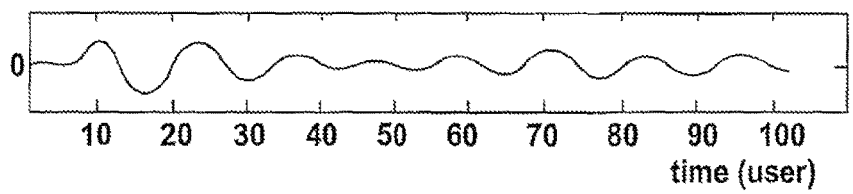
Figure 18:
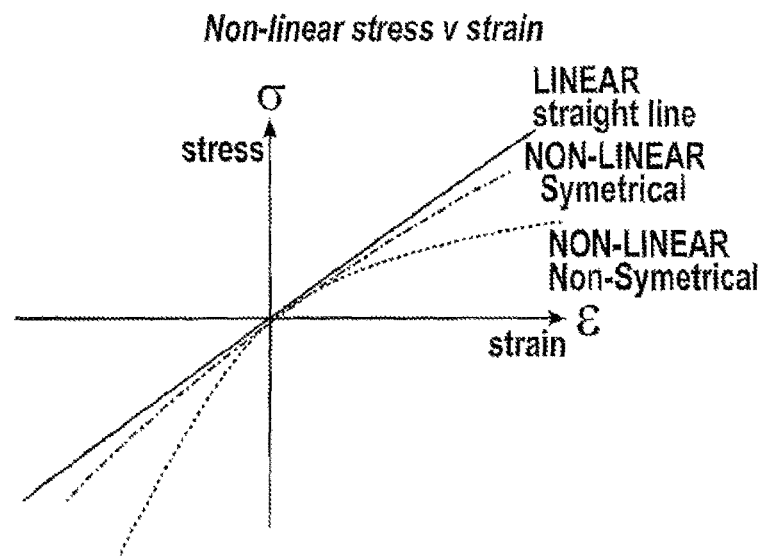
Figure 19:
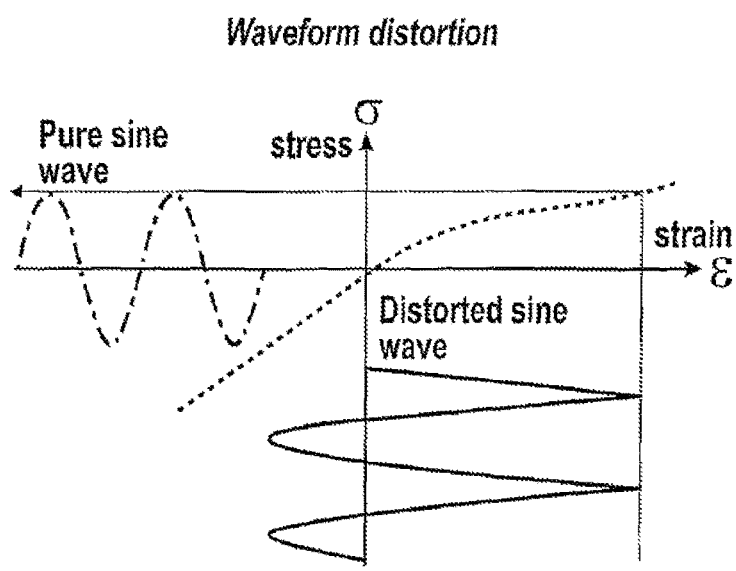
Figure 20:
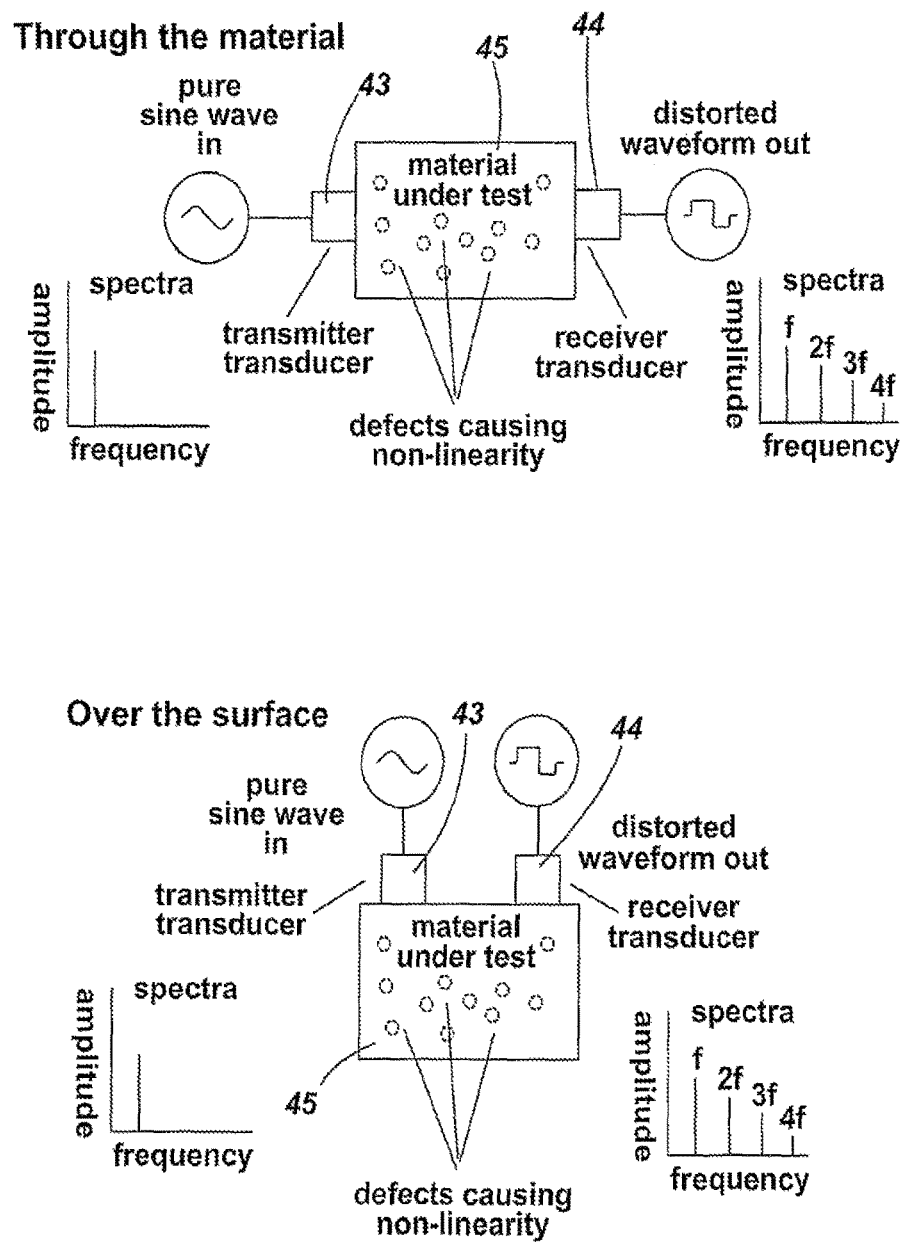
Figure 21:
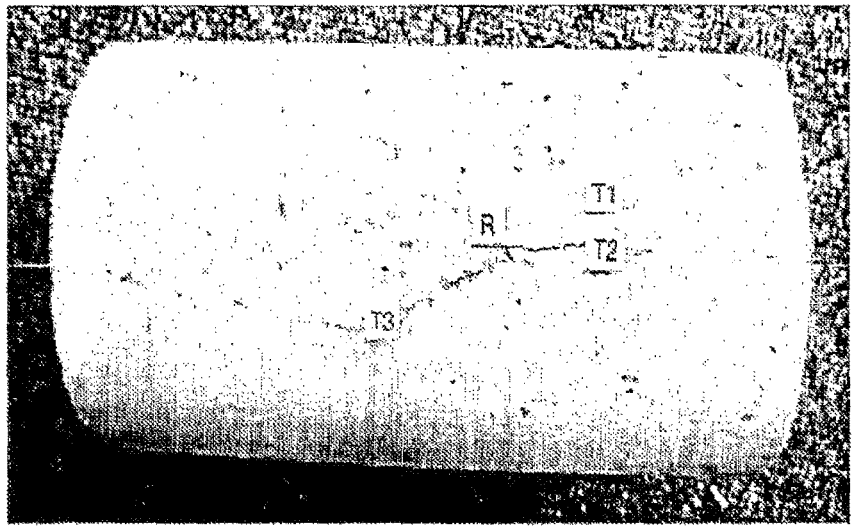
Figure 21:
Figure 22:
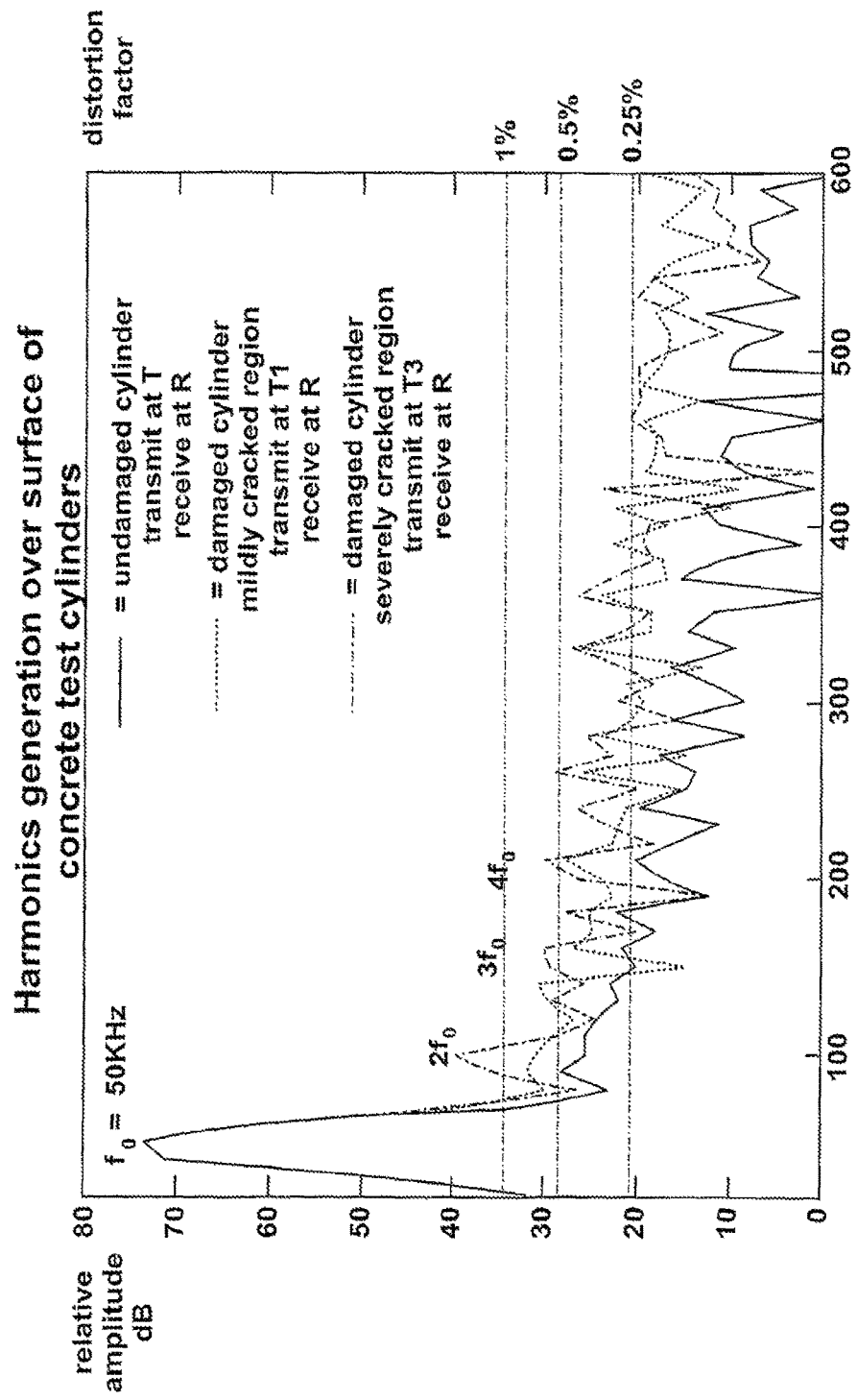
Figure 23:
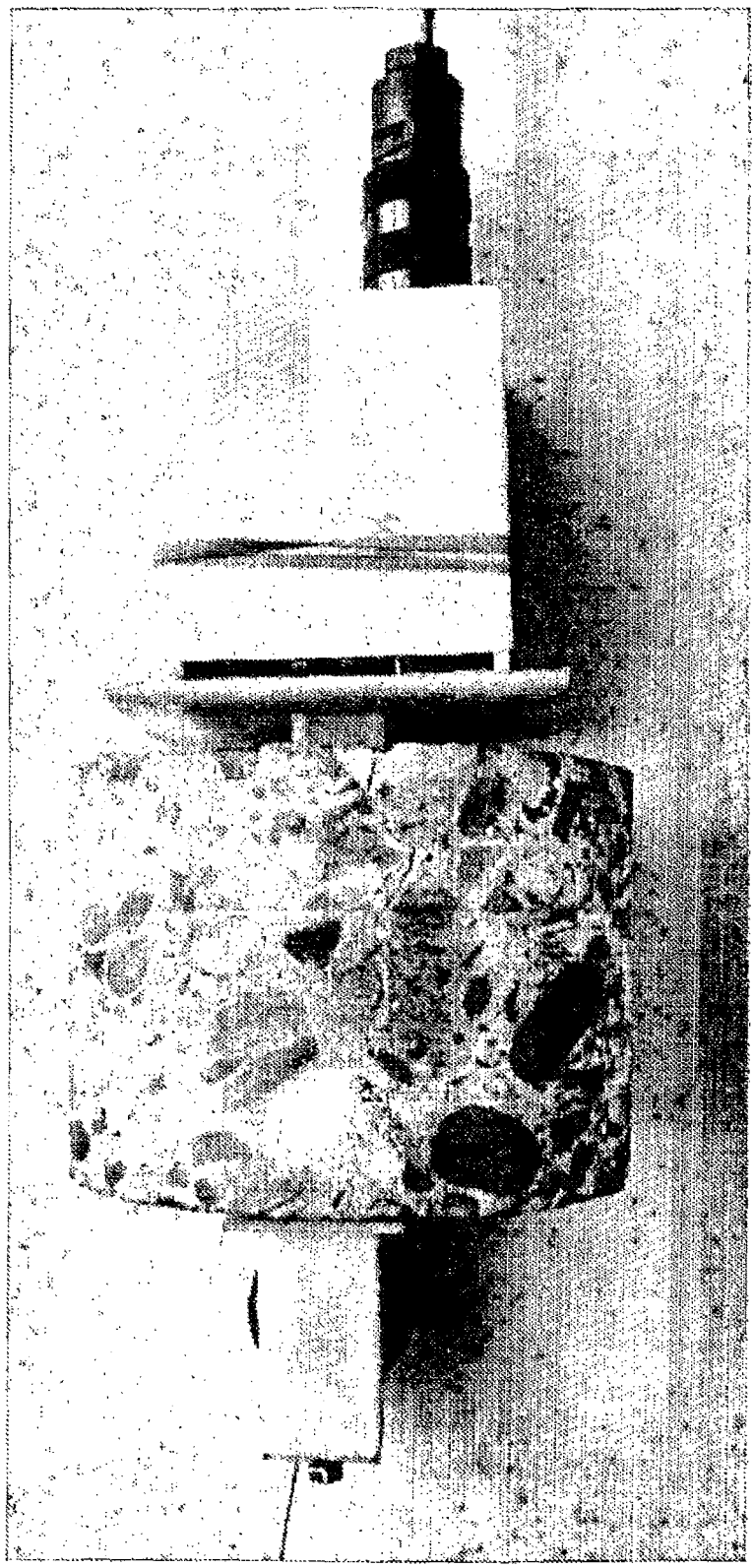
Figure 24:
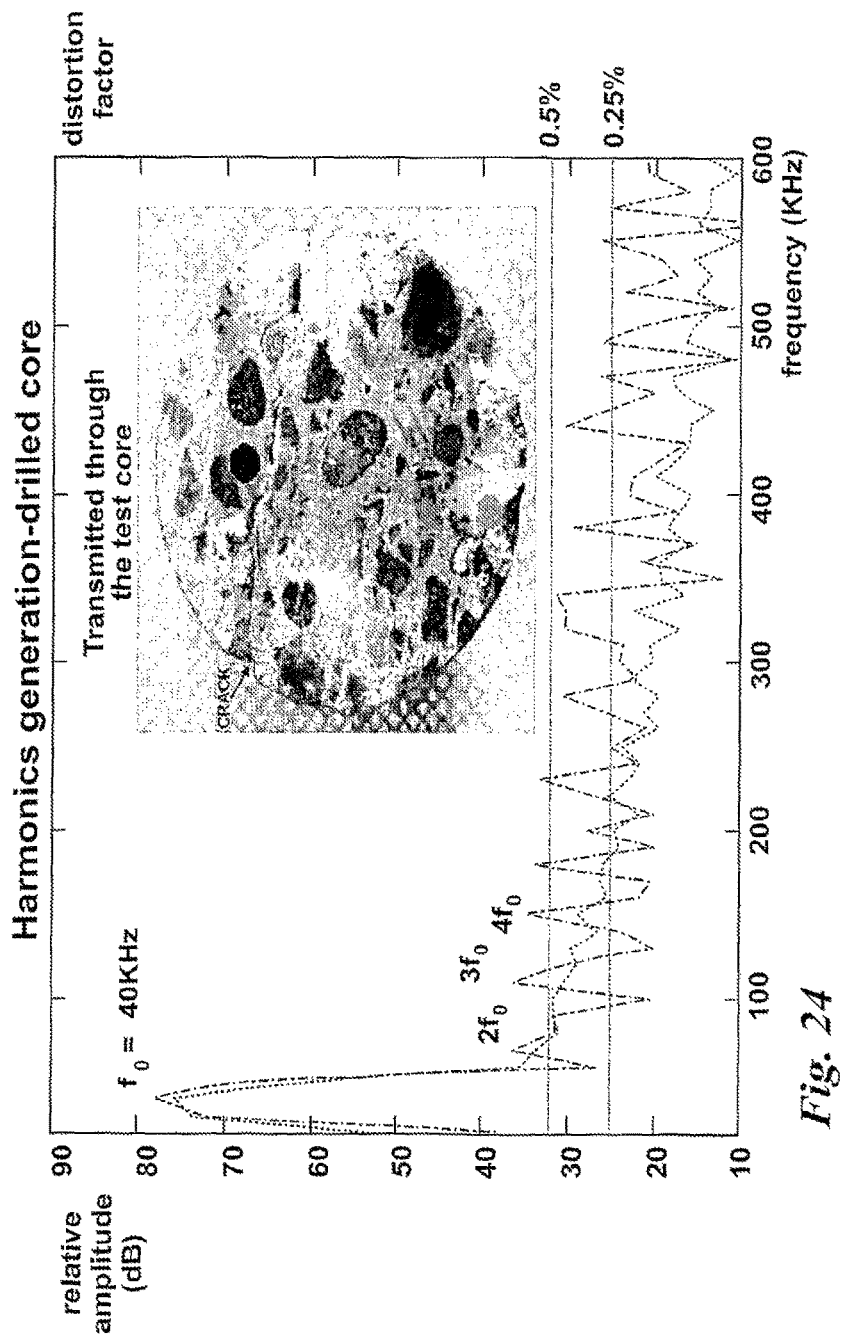
Figure 25:
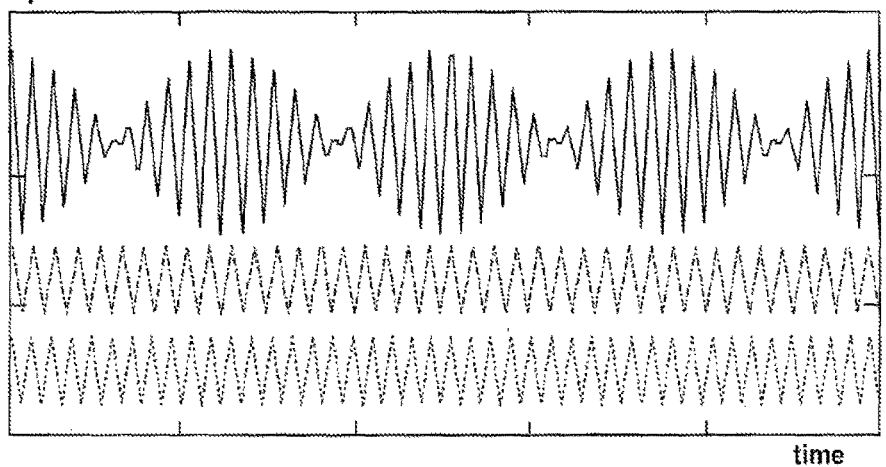
Figure 25:
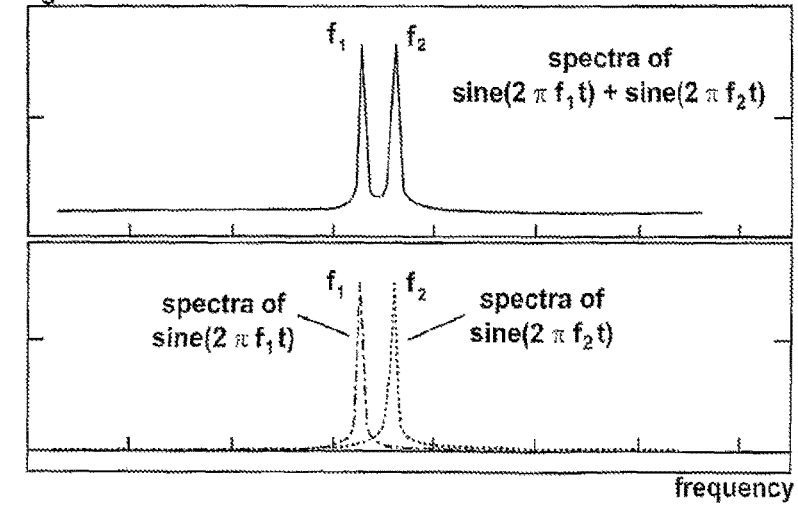
Figure 26:
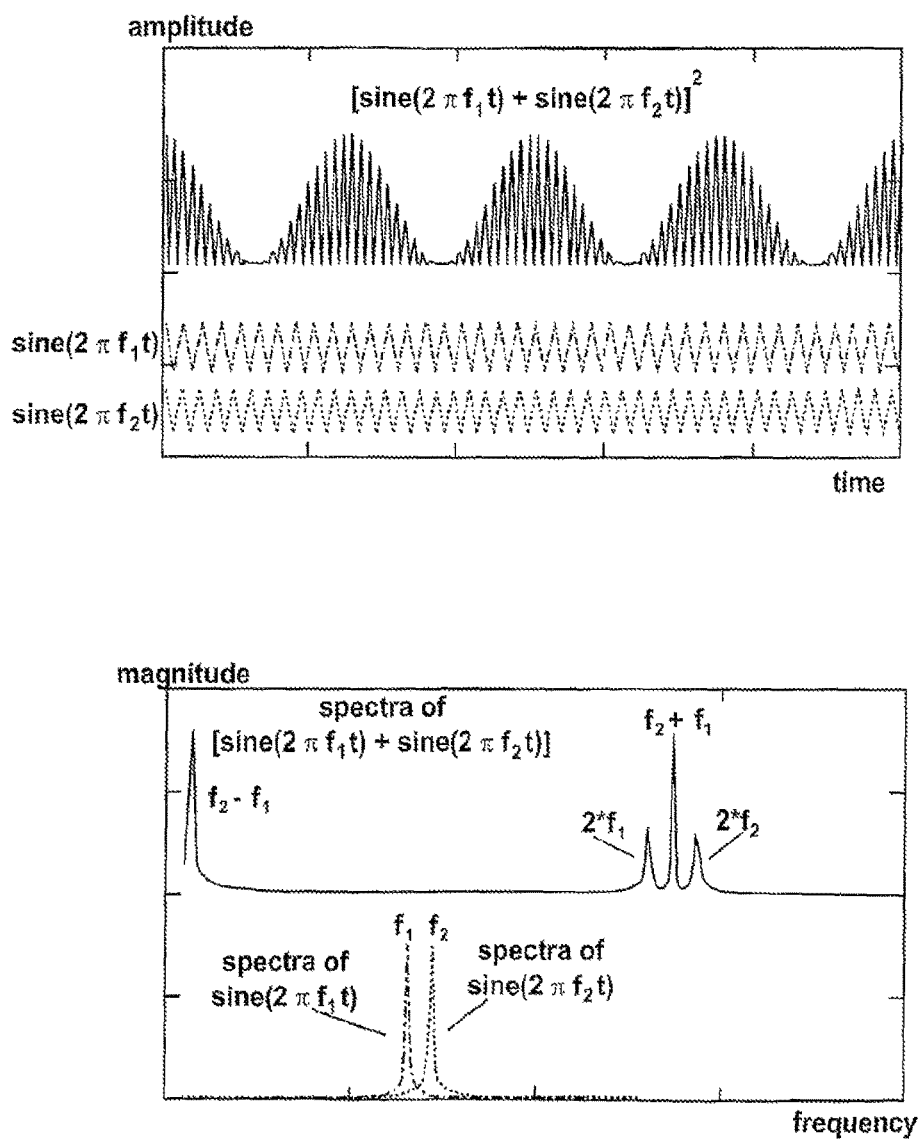
Figure 27:
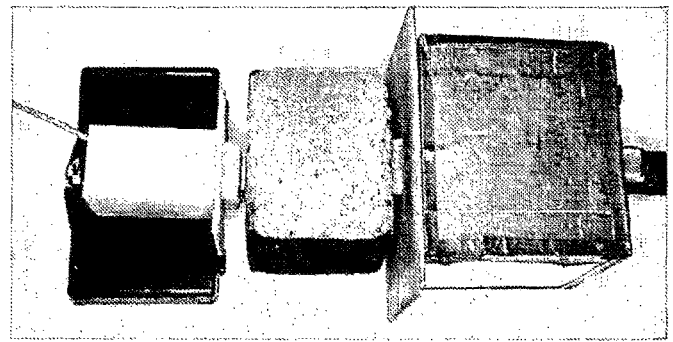
Figure 27:
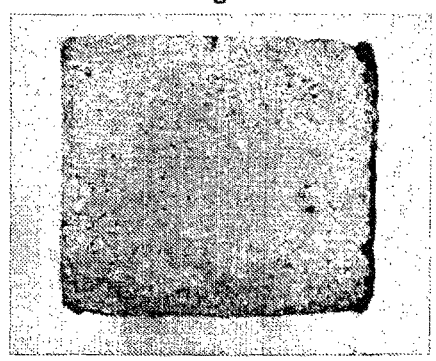
Figure 27:
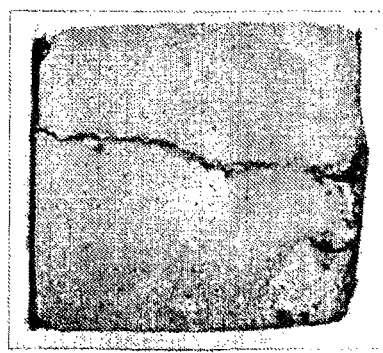
Figure 28:
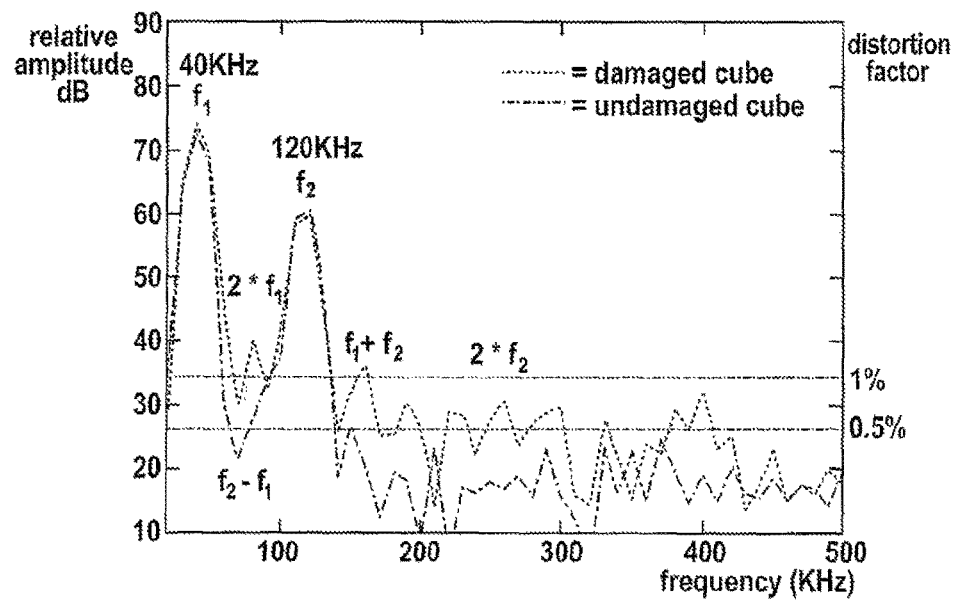
Figure 28:
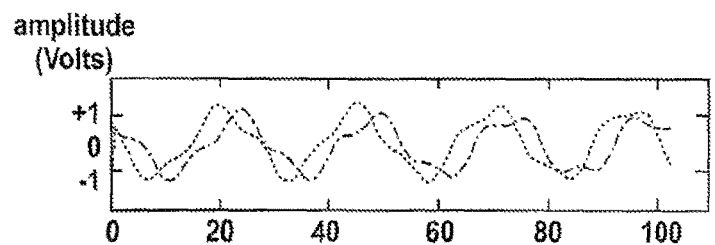
Figure 29:
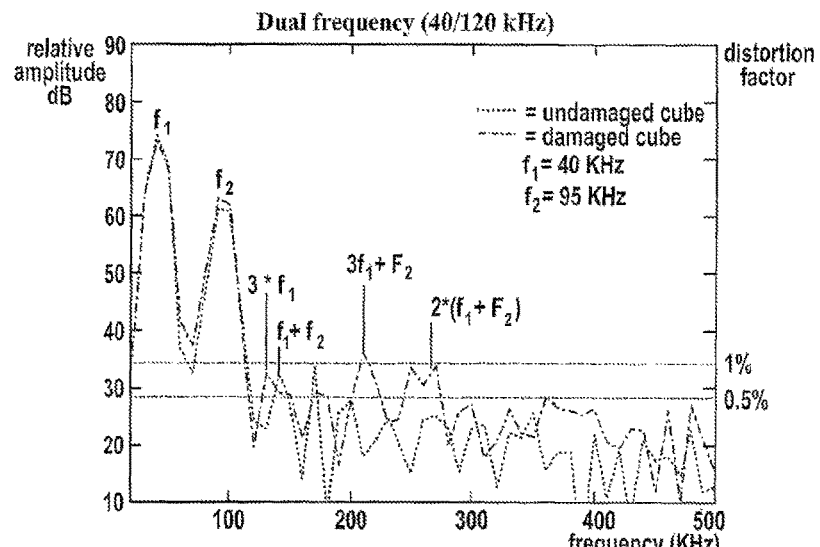

FIGS. 13(a) to (c) show a number of device locations on the test workpiece, which incorporates a defect;

FIGS. 14(a) to (c) show the corresponding outputs;

FIGS. 15(a) to (g) illustrate the output of a transducer device in sensor mode for a workpiece which is stimulated by a transducer device in transmission mode with increasing loading on the workpiece;

FIGS. 16(a) to (d) form a sequential description of time reversal defect detection;

FIGS. 17(a) to 17(d) show waveforms connected with another embodiment;

FIG. 18 is a graph illustrating non-linear stress v strain;

FIG. 19 is a graph showing the resultant wave form distortion;

FIG. 20 illustrates schematically transducer configurations on concrete samples;

FIG. 21 is photographs of cracked and undamaged concrete samples;

FIG. 22 shows test results from the samples of FIG. 21;

FIG. 23 is a photograph of a concrete sample prepared for testing;

FIG. 24 illustrates test results from the sample of FIG. 23;

FIG. 25 shows the combination of two sine waves;

FIG. 26 illustrates the inter-modulation products resulting from the use of combined sine waves;

FIG. 27 illustrates a test configuration and test samples;

FIGS. 28 and 29 are test results of test on the samples of FIG. 27; and

Figure 31:
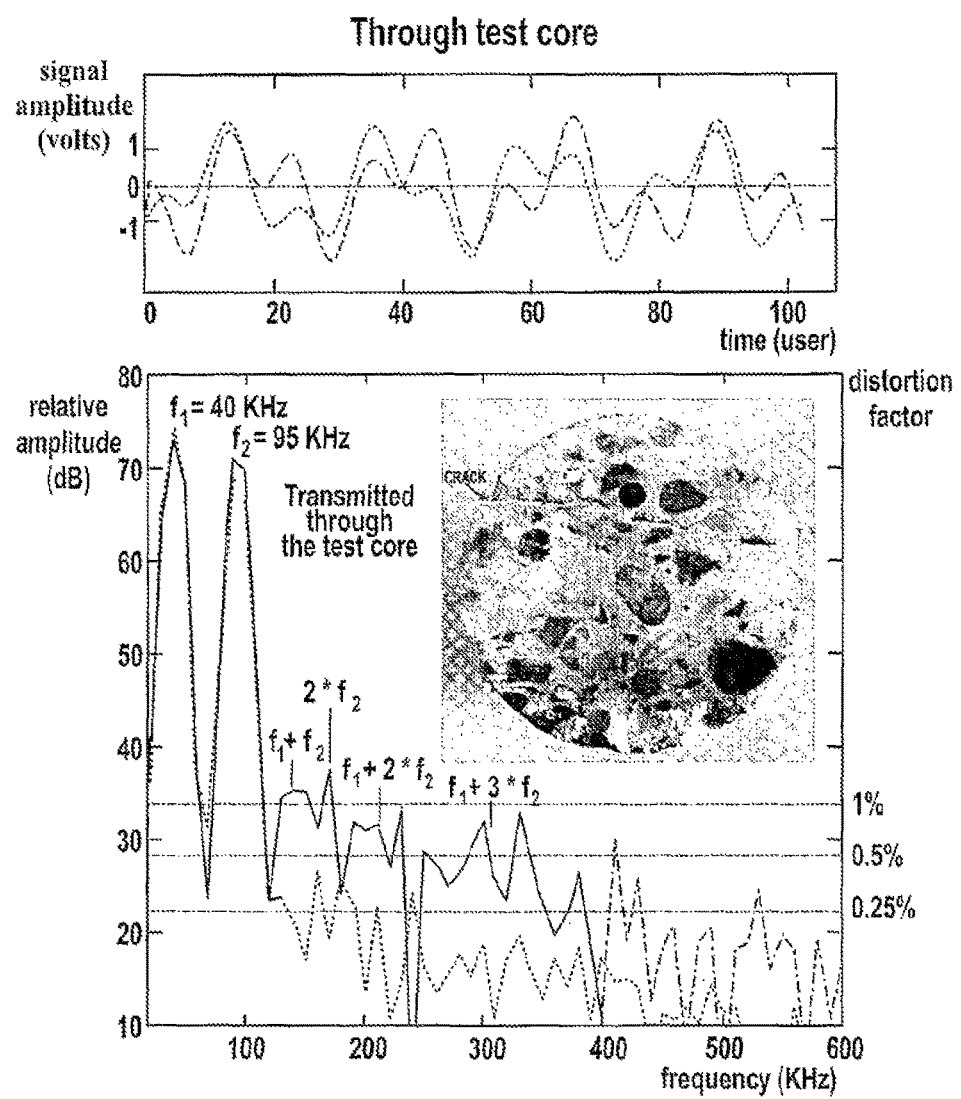
Figure 32:
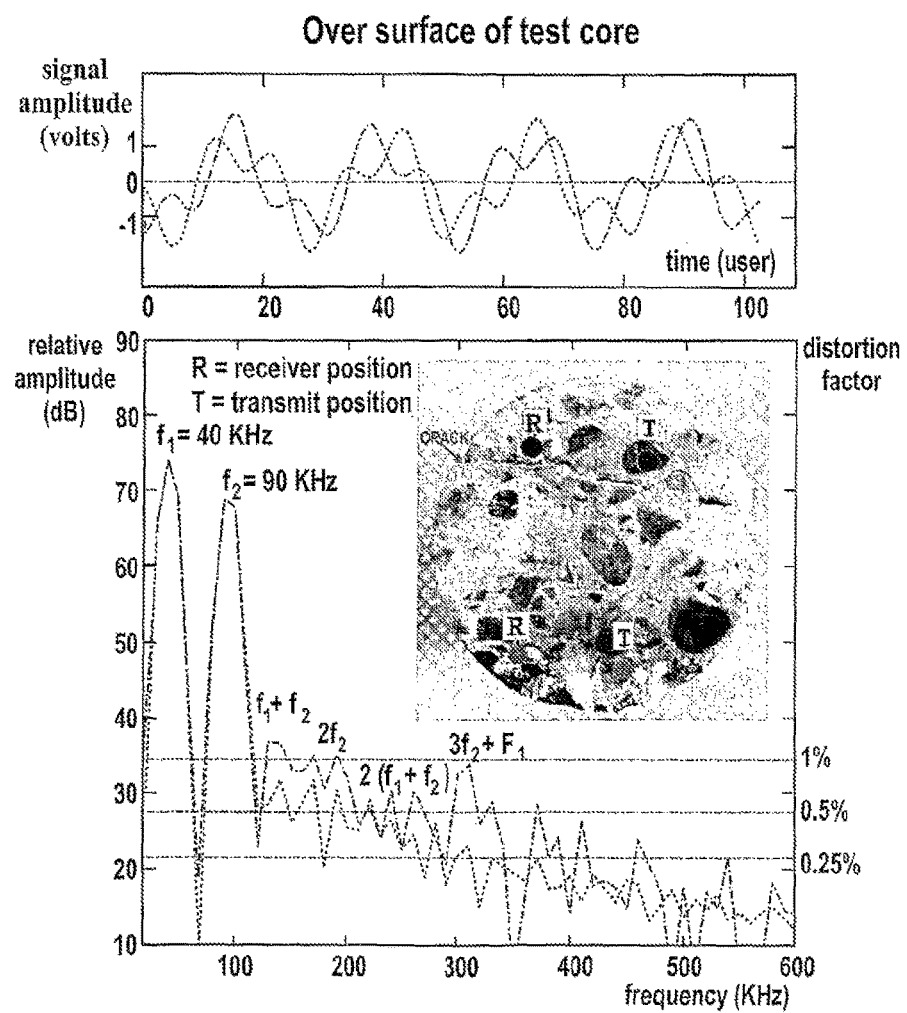
Figure 33:
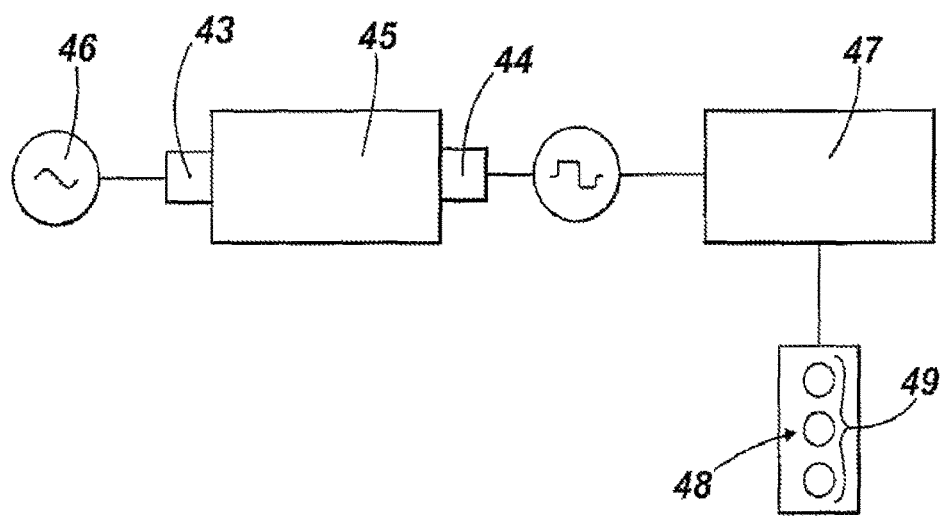

FIGS. 31 and 32 show comparable results for a through core test and a surface core test respectively; and FIG. 33 is a schematic circuit of a detection device.

Ultrasonic techniques for detecting defects in workpieces are well known and a variety of transducers are utilised. In most arrangements, at least, an ultrasonic transducer is passed over the surface of a workpiece sending ultrasonic pulses into the workpiece and the reflected signal is detected. In other examples a transmitter is placed at one location on a workpiece and one or more receivers on the workpiece detect the resultant signal.

In general the transducers and receivers are designed very specifically for a particular purpose and tend only to be able to handle a narrow band of signals. The techniques used can also be very workpiece specific. Problems have also been encountered when trying to use such techniques with composite materials.

Many of these issues have come together in connection with aircraft, where integrity testing is extremely desirable but there is an increasing usage of composite materials in order to reduce weight and increase fuel efficiency. A number of proposals have been made, including the use of finely tuned embedded transducers but these approaches tend to be very expensive, rather component specific and can require excessive computation in order to discriminate the results.

There is a need for transducers and methodology which is more flexible, and in particular, is capable of determining whether or not a component has a defect both quickly and easily.

The Applicants have developed a number of approaches in this connection, which are in part based on the insight that if they could configure a broadband ultrasound transducer, which could be operated either as a transmitter or a receiver then it would be possible to implement a wide range of techniques, which the user could select in accordance with the issues that needed to be dealt with. By rendering the device such that it could be used in an analogue/digital mode, it would also be possible to arrange a number of such transducers on a common data bus overcoming many of the transmission problems, which currently exist, particularly as radio transmission of data is not generally possible in connection with aircraft.

Figure 6:
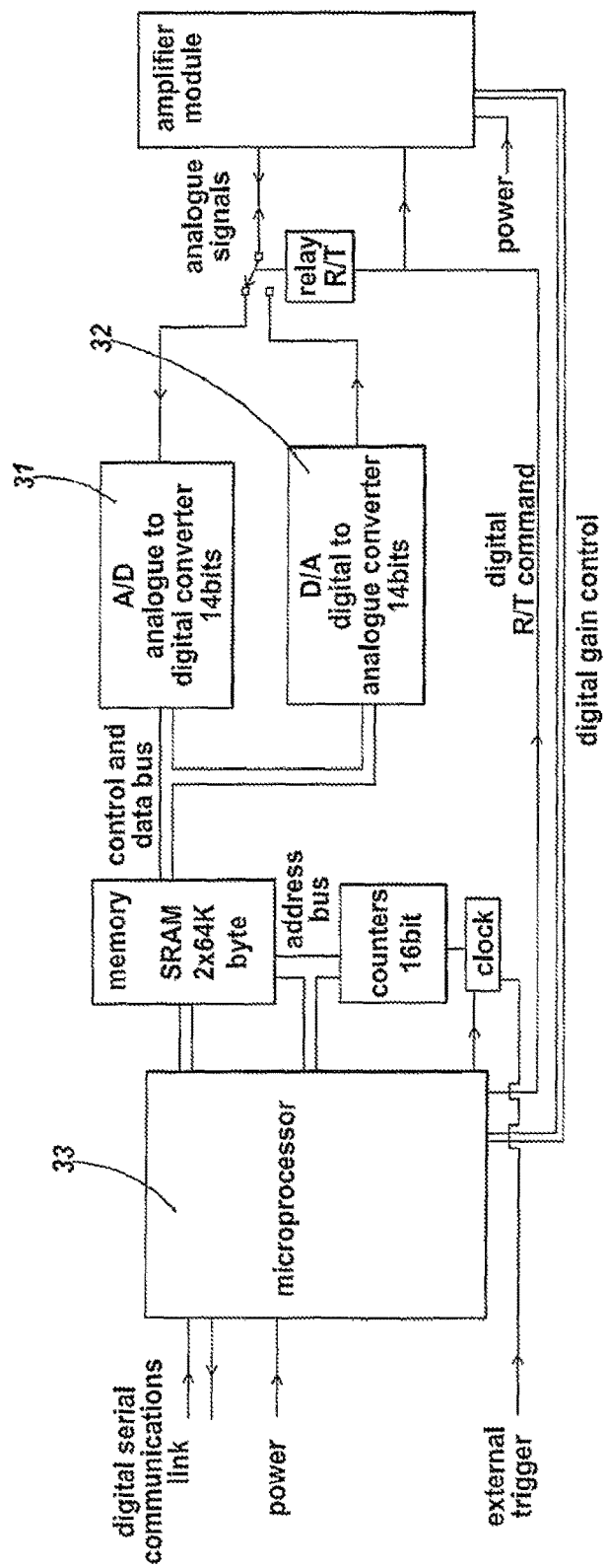

It should be appreciated that the device is capable of being pre-programmed with the desired waveform data and consequently able to transmit a variety of complicated waveforms, some examples that have been evaluated are sine wave bursts of a specific duration, sine wave sum bursts and frequency sweeps. Referring to FIG. 6 the microprocessor 33 is connected to SRAM memory which is addressed by an independent counter, the A/D converter 31 or the D/A converter 32 directly accesses this memory when the device is either sampling a received signal or transmitting a pre-programmed waveform, the counter being incremented for each data sample received or transmitted. A particular advantage of this arrangement is the counter can be made to count in reverse, that is decrement. This has direct applications for time reversal methods whereby the received signal data that has been recorded in the memory is transmitted back into the workpiece in reverse time order, the advantage being that data need not be transferred to and from any other device. Additionally the method of using an independent counter allows for very accurate synchronisation between devices since the counts can be initiated simultaneously independently of the microprocessor. The transmitted waveform and all the received signals are recorded at precisely the same time, there is little or any data skew.

The microprocessor can implement a pre-determined series of count instructions to the counters, thereby allowing the data to be fetched or loaded in any part of the memory space. This method can be usefully employed when using time reversal techniques that require the data to be filtered for harmonic content.

Figure 1:
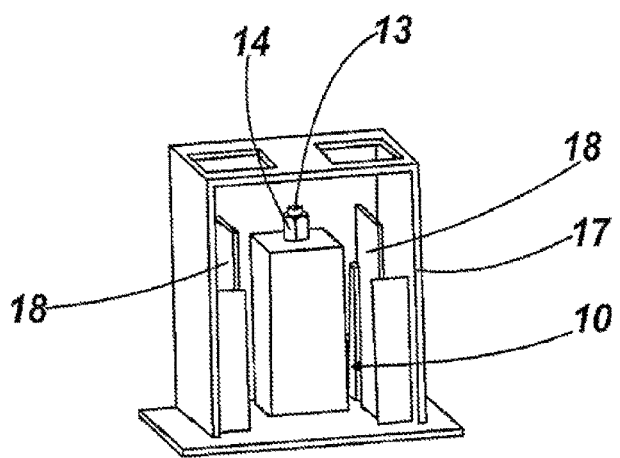
FIG. 1 is a stylised view of a transducer unit.
Figure 2:
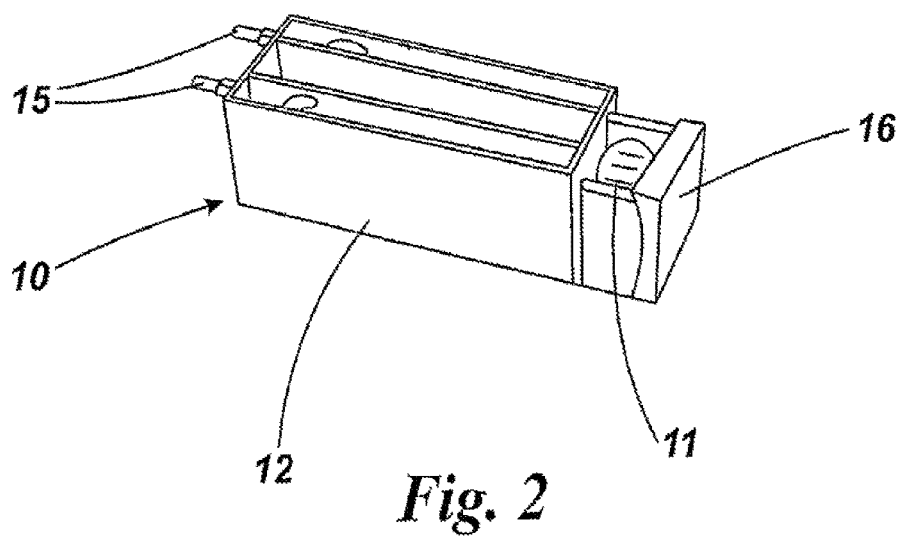
FIG. 2 is a picture of a transducer unit for use in the device of FIG. 1.

FIGS. 1 and 2 illustrate aspects of a basic transducer assembly.

As can be best be seen in FIG. 2 the transducer 10 comprises a piezoelectric crystal 11 mounted on a tungsten epoxy backing 12. A spring loaded threaded nylon rod 13 and nut 14 is used to secure the transducer into its housing and provide a force when the transducer is placed in contact with the work piece. Electrical connections 15 also pass through the backing 12, whilst a matching front plate 16 is mounted on the front surface of the crystal 11.

The piezoelectric is preferably composed of a epoxy/PZT composite and the ratio of PZT to Epoxy can be changed to match the workpiece material. For example the workpiece is made of aluminium, aluminium has an acoustic impedance of 12MRayls and the PZT/Epoxy element has also 12MRalys acoustic impedance, and likewise the tungsten/

Epoxy backing material has an acoustic impedance of 12MRayls. With this arrangement it is unlikely that there will be internal reflections within the transducer, since they all acoustically match. It is this that gives the wideband properties of this type of transducer.

The tungsten, in the epoxy, has typically been made of spheres of a single size according to the frequency at which the transducer has been intended to be used. However, for lower frequencies, where large spheres are required, this has been particularly unsuccessful because only a limited number of spheres per unit volume could be inserted. The Applicants have realised that they can overcome the restricted frequency range of such transducers by having a range of sphere sizes, which not only enables them to achieve the desired density of tungsten, but also provides spheres of requisite size for different frequencies. For example a backing block containing tungsten particles of 250, 25 and less than 1 micron diameters has provided a particularly practical transducer. The semi-rigid nature of the nylon rod 14 is also efficacious as this would not introduce resonators in the backing.

Figure 3:
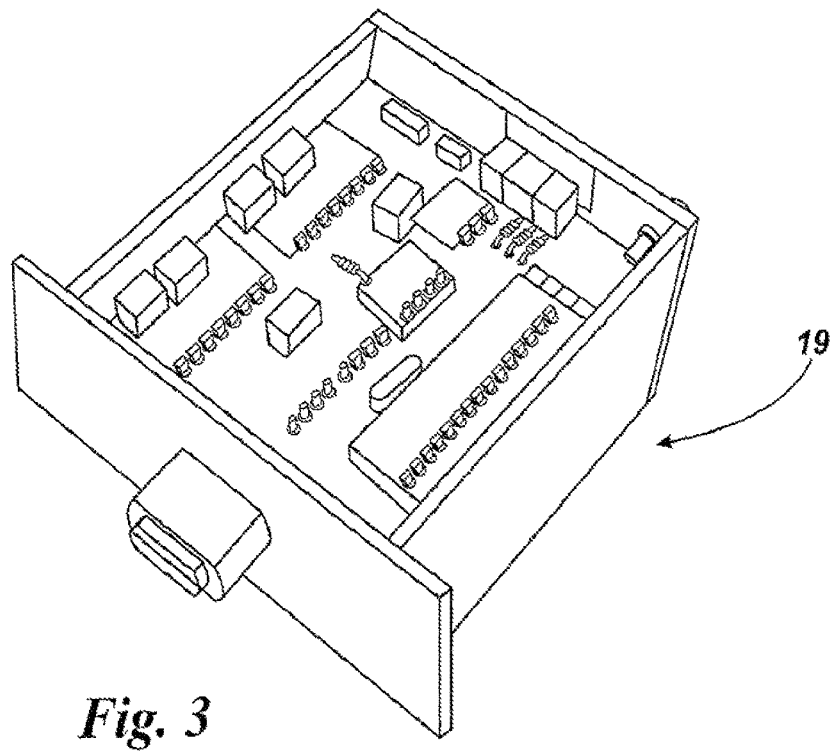
FIGS. 3 and 4 are views from above and below respectively of an actual unit of the type illustrated in FIG. 1.
Figure 4:
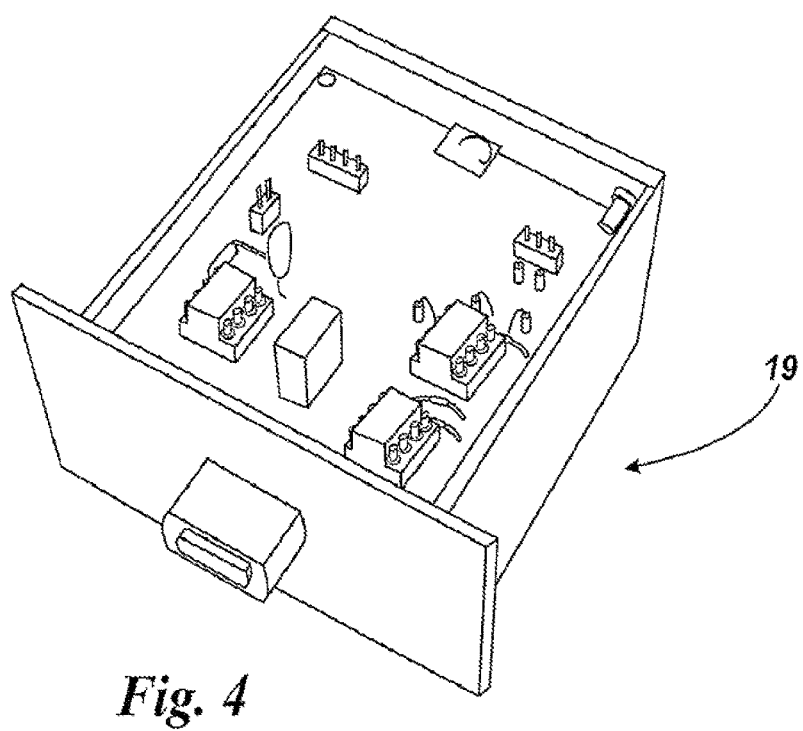

As conceived, the transducer 10 is mounted in a frame 17, with associated circuit boards 18. Examples of such overall box assemblies are shown, indicated 19, at FIGS. 3 and 4.

Figure 5:
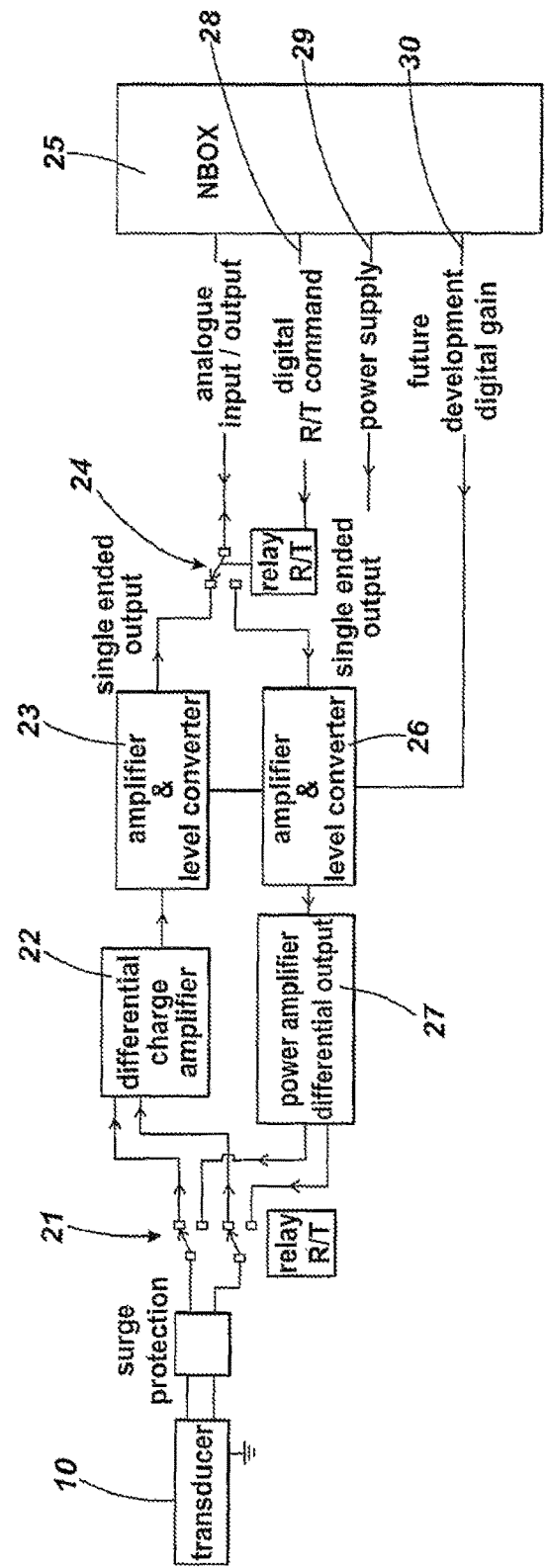
FIGS. 5 to 8 illustrate a variety of electronic configurations for use in the device of FIG. 1.

FIG. 5 shows the circuitry for one such arrangement 19, where analogue signals are utilized throughout for the signal processing. The transducer 10 can receive and transmit signals to relay controlled multiple pole switch at 21. If it is acting as a receiver, then the switch is connected as shown in FIG. 5 and its output signal passes to a differential charge amplifier 22 and thence to another amplifier and level converter 23, whose output is fed to a further switch 24 and thence to an interface 25, which can be connected to a data bus. If the transducer is in transmit mode, switches 24 and 21 are switched to form a separate channel. In this case the transmission signal passes through an amplifier and level converter 26 and a power amplifier differential output 27 and thence to the transducer 10 through switch 21. The position of the switches 21, 24 is controlled from the interface 25 on output 28 and the interface also provides the necessary power supply at 29. It may also adjust the gain of the amplifiers 23, 26 on output 30.

It will be understood that because the transducer 10 can operate on a broadband and because it can be remotely configured as a transmitter or a receiver via the interface 25, the Applicants have created an extremely flexible arrangement for use in defect detection.

FIG. 6 shows the corresponding arrangement in which the signals to be transmitted or received are respectively analogue to digitally or digitally to analogue converted by the respective converters 31, 32, with the microprocessor 33 acting as the interface. The transducer is connected to the amplifier module, which essentially substitutes for components 22, 23, 26 and 27 in FIG. 5. It will be understood that the advantage of using digital signals is that it is easier to communicate these with a central computer.

Figure 7:
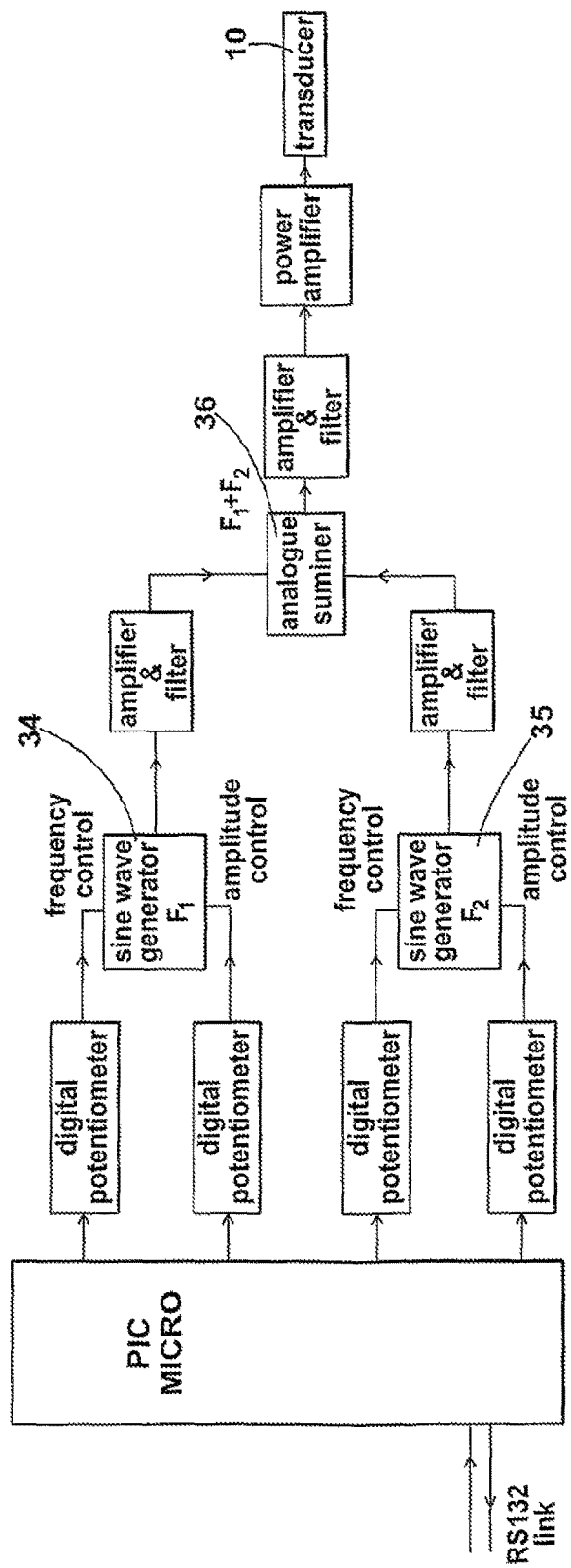

FIG. 7 shows a further development in which the control circuitry includes sine wave generators 34, 35 for generating respective frequencies in $F_1$ and $F_2$. These can be summed together at 36 for embodiments where it is desirable for the transducer 10 to transmit two frequencies simultaneously.

Figure 8:
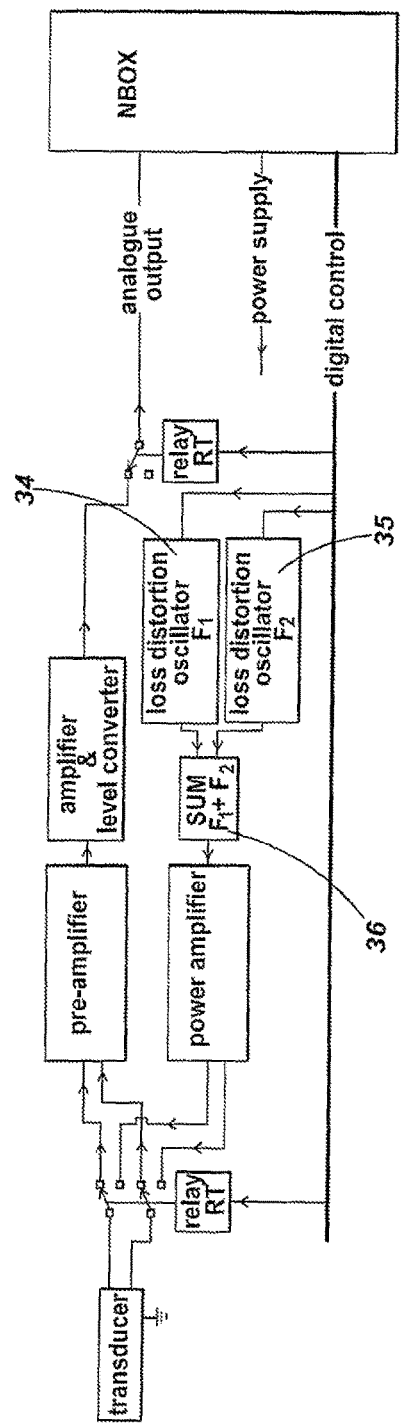

FIG. 8 shows a similar "analogue" version for transmitting signals $F_1$ and $F_2$ and otherwise corresponds to FIG. 5.

FIG. 9 illustrates a basic system configuration. Two units 19 are applied to a workpiece 37 with the right hand one set to transmit and the left hand one set to receive. They are connected to a communication link 38, e.g. a data bus which is in turn connected to a local computer 39, which may be connected to other computers or a mainframe computer by an internet connection 40.

FIG. 10 illustrates an alternative arrangement which is essentially the same as FIG. 9 except that at 41 a unit 19 is used to operate either an actuator or a hammer schematically illustrated at 42.

Figure 11:
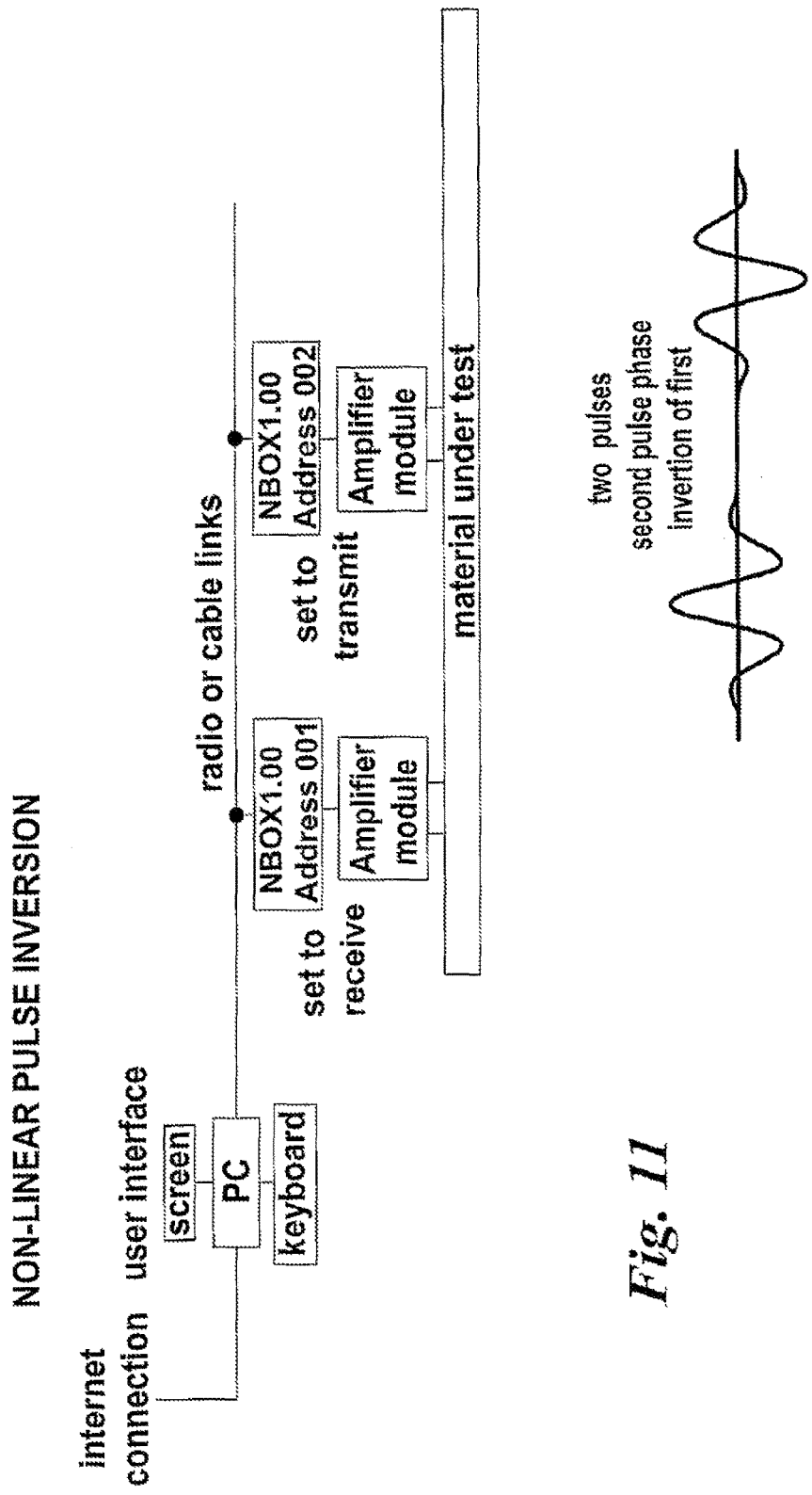

FIG. 11 exactly corresponds to FIG. 9 but recognises the possibility of transmitting two pulses.

Figure 12:
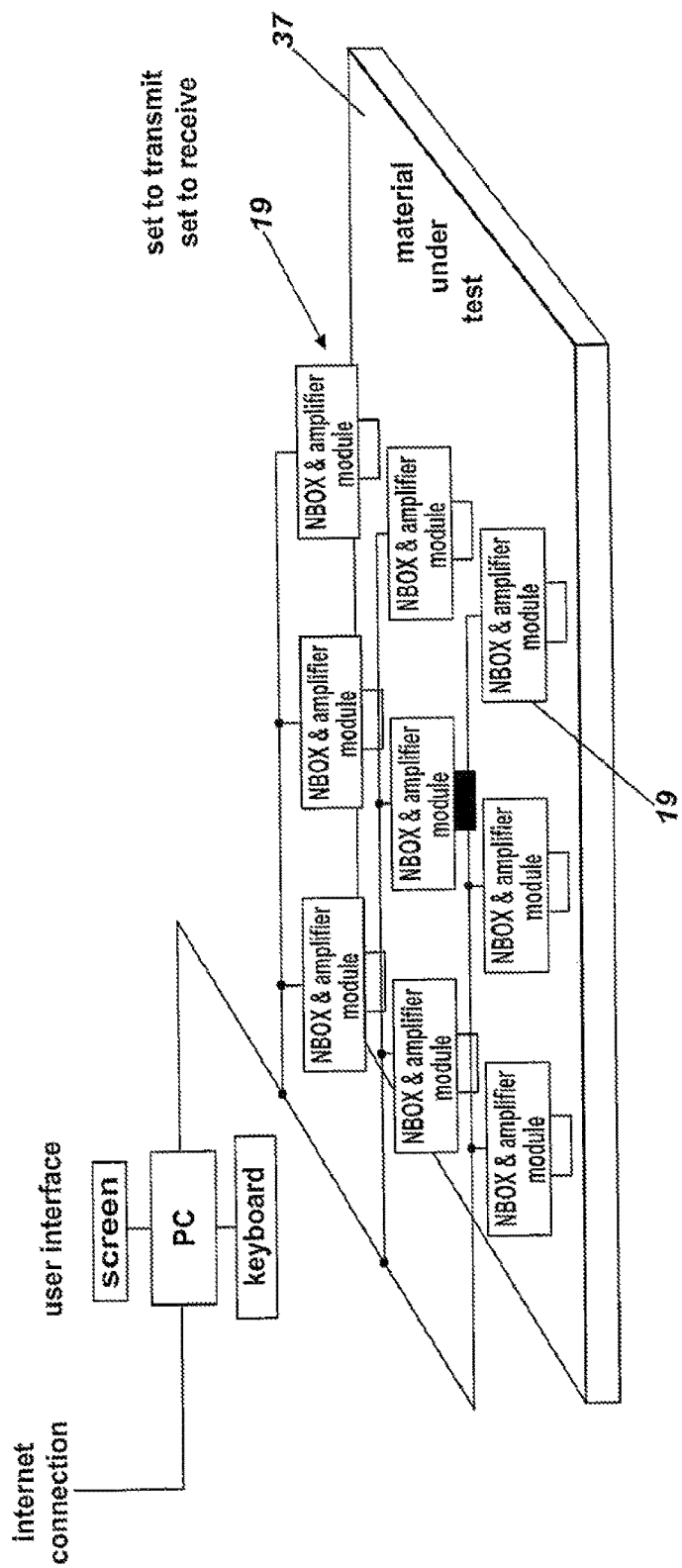

FIG. 12 illustrates units 19 configured in an array across the workpiece. In the particular set up illustrated the central unit 19 is set to transmit and the surrounding units are set to receive. It will be appreciated that a variety of arrays can be built up, for example five by five.

As will be understood by a man skilled in the art, the basic configuration illustrated in FIG. 9 could be used in a typical industry way wherein the unit 19 set to transmit transmits a suitable resonant frequency an the receiving unit records the resonant decaying signal. If there is a defect there will be a shift in frequency as the amplitude decays.

A person skilled in the art will also be familiar with the concept of time reversal, but for convenience this is set out in FIG. 16. The Applicants' ability to build extremely flexible arrays with transducers which can operate both as receivers and transmitters makes the achievement of time reversal much more than a theoretical possibility and enables the initial pilot signal (the source in FIG. 16) to be generated at any point in the array. Further the Applicants have realised that if the time reverse retransmission is made at high power then considerable energy will be delivered at the point of origin of the source. In this way highly focused energy can be provided at any point on the surface of the test material underneath the array. If there should be a defect at the refocusing position itself, then harmonics will be generated and these will be observed by the surrounding units 19 as well as the unit at the refocusing point.

Returning to the FIG. 9 configuration, it will be understood that the relationship between the units 19 in their respective transmit (T) and receive (R) modes with the defect can be any of the instances illustrated in FIGS. 13(a), (b) and (c). Corresponding outputs are shown in FIGS. 14(a), (b) and (c). It will be particularly noted that in FIGS. 14(a) and 14 (b) the third harmonic initially rises sharply under low impact, but then falls away as the second harmonic rises under higher impact. It is considered that the rising third harmonic indicates where the workpiece is in a condition of micro-cracking, but when delamination occurs then this falls away and the second harmonic rises rapidly. The Applicants have therefore developed an approach which enables the detection of micro-cracking and distinguishing this from the onset of de-lamination. They are not aware of any other system which can achieve this. The effect is also illustrated in the graphs of FIG. 15.

FIG. 17 illustrates another mode of operation in which two impulses of equal frequency and amplitude but phase shifted 180° are transmitted. FIG. 17(a) shows the received signals from the workpiece which are generated by the impulses and FIG. 17(b) shows their summed output. FIGS. 17(a) and (b) illustrate the situation where there is no defect. In contrast FIGS. 17(c) and (d) are the corresponding results where there is a defect. It will be noted that in FIG. 17(d) there is a clear output, whereas in FIG. 17(b) the signal is essentially null. This process thus very quickly provides a readable output showing the existence of a defect, without the need for extensive frequency analysis using extensive computation and time. In an alternative arrangement a ratio is generated from the respective maximum amplitude of the signals. The value of the ratio is indicative of the presence or absence of a defect.

It is observed that the waveform at (a) is essentially triangular, whereas at (b) the waves are more in the form of a sine wave. It is believed that this is a result of the undamaged carbon fibres in the test piece being locked up by each other, hence producing the triangular wave but when damage has occurred, they are more free to move and the sine wave output results. The degree of transition between the two wave forms may provide an early indication of damage.

The wide bandwidth of the transducers, in, for example the FIG. 9 configuration, enables the transducers to pick up sidebands. The presence of these sidebands has also been determined to be an indication of damage and they can be quantified using a modulation index. These sidebands are usually generated where two frequencies are transmitted. They can either be transmitted from a single transmitter 19, using the circuitry described earlier, or two separate transmitters can be utilised.

In the arrangement shown in FIG. 10 the use of a high power actuator to flex a workpiece and thus open and close a defect is known, but driving it using a unit 19 is particularly efficacious, because it enables it to be readily incorporated into the control system as a whole.

Where an impact hammer is utilized, it is currently typical to determine the resultant change in frequency in the decaying pulse using Fourier analysis of "windows" of part of the waveform and this is very time consuming. The Applicant is proposing that the received signal should be passed through a phase lock loop, which uses the input frequency as the reference frequency and then the feedback signal can be monitored, because it will be indicative of frequency change. Thus a frequency deviation will be given in real time.

A loudspeaker may also be used to bring the workpiece up to resonance and, then after the input is discontinued the frequency shift can be measured as the workpiece's vibration dies down.

A laser interferometer may be used to measure the workpiece's resonant frequency before the loudspeaker is applied.

The resonant frequency is applied to bring the workpiece up to a high amplitude oscillation. The loudspeaker is then turned off and the frequency shift measured as the oscillation dies away.

The testing of concrete structures has poses many of the same problems. Conventional ultrasonic transmission and pulse echo methods have limitations due to the nature and composition of concrete since they cause multiple reflections and nondirect ray paths.

Nonlinear acoustic methods seek to determine how an ultrasonic waveform changes when it propagates through or over the surface region of a medium. These changes are directly related to the stress strain relationship and the hysteretic properties of a material and are not unduly effected by the ray path. In damaged materials, particularly ones that have microcracking, the stress strain relationship does not obey Hooke's Law of elasticity, stress is not proportional to strain, it is not linear. In addition these materials often have a stress strain relationship that is nonsymmetric, that is the reaction to compressional forces will have different properties to that of tensile forces, this is a result of the cracks opening and closing under a tensile or compressional loads.

The stress strain curve for nonlinear behavior is illustrated in FIG. 18. The result of nonlinearity is that any stress loading that is in the form of a pure sine wave will produce a strain that is distorted as it traverses the material. This is illustrated in FIG. 19. As has been mentioned the degree of this distortion is measured by examining the spectral content of this distorted waveform, second, third and higher harmonics will be present and are related to the amount of damage. Greater sensitivity to nonlinear effects can be achieved by transmitting complex waveforms into the material, for example a waveform that is composed of the sum of two sine waves. Any non linearity will act to produce a multitude of frequency components in the spectra, called intermodulation products. Considerable practical advantages can be made if only one transducer is used to transmit these complex waveforms. To achieve this, wideband transducers that are acoustically matched to the test material were developed that do not generate nonlinear effects internally or at the point of contact with the concrete, these transducers were used in the experiments detailed in this paper.

The simplest method in a practical system that measures nonlinear effects in a material using acoustic waves is to measure the harmonics generated when a pure tone (pure sine wave) is transmitted through or over the surface of a material. This is illustrated below in FIG. 20 where a transmitter 43 and a receiver 44 are mounted on a workpiece 45.

The harmonics are measured by examining the power spectra of the received signal. The transmitted frequencies (fundamental) amplitude is compared to that of the amplitudes of each of the harmonic frequencies. These harmonics are expressed in terms of decibels (dB) down from the fundamental, that is the number of decibels below the fundamentals amplitude. These values can be converted to a distortion factor that is expressed as a percentage.

Other nonharmonically related frequencies may also be generated by the sound wave, particularly in the presence of severe defects, these are called overtones and noise they result from acoustic emissions, hysteresis and other effects.

FIG. 21 below shows the photographs of two concrete test cylinders (size 300 mm long, 150 mm diameter). FIG. 22 below shows the results obtained by sending a 50 kHz sine wave over the surface of these two cylinders of concrete. The second harmonic generated in the severely cracked region is clearly visible and has a level of distortion above 1%. The third and fourth harmonics are not so prominent but have values above 0.5%. The undamaged concrete sample does not produce any clear harmonics and consists of noise predominately below 0.25%.

The photograph in FIG. 28 shows a microdamaged drilled test core with an ultrasonic transmitter on the right and a receiver on the left. The blue trace of the spectral plot in FIG. 24 shows that transmitting and receiving in a line through the concrete close to the crack produces relatively high levels of 2, 3 and 4, harmonics above 0.5%. Transmitting and receiving in a line away from the crack (shown in red) produces little harmonic content.

If two sine waves of different frequency are added together the resulting power spectrum is unaltered, this is illustrated in FIG. 9 below.

An ultrasonic wave composed of the sum of two sine waveforms of different frequencies, f1 and f2 with equal amplitude, can be represented by [sine(a)+sine(b)], where $a=2\pi f1 t$ and $b=2\pi f2 t$. If this waveform is passed through a material that exhibits a square law stressstrain relationship.

The resultant wave forms can be expressed as:

$$A(t)=[\sin(a)+\sin(b)]^2$$

by expansion this gives:

$$A(t)=\sin^2(a)+2\sin(a)\sin(b)+\sin^2(b)$$

using the standard trigonometric identity formulae . . . sin(a)·sin(b)=½[cos(ab)−cos(a+b)] and noting that sine(a)·sine(a)=½[cos(aa)−cos(a+a)]=½[cos(0)−cos(2a)] which becomes=½[1−cos(2a)], since cos(0)=1, then the expression for A(t) becomes:

$$A(t)=\tfrac{1}{2}[1\cos(2a)]+[\cos(ab)\cos(a+b)]+\tfrac{1}{2}[1\cos(2b)]$$

rearranging $$A(t)=1+\cos(a\,b)\cos(a+b)-\tfrac{1}{2}\cos(2a)-\tfrac{1}{2}\cos(2b)$$

FIG. 26 below shows a graphical representation of this process. Four distinct frequencies and one constant term are generated by this process, the frequencies are; the second harmonics of f1 and f2 that is (2*f1) and (2*f2). The sum and difference frequencies of f1 and f2, that is (f1+f2) and (f1 f2). The second harmonics are half the amplitude of the sum and difference frequencies.

As there is a larger variation in the generation of the sum and difference frequencies these should provide greater sensitivity in the indication of non-linearity. If the sine wave sum is subject to nonlinearity that is of a higher order than a square law stressstrain relationship then many other multiples, sum and difference combinations result, these will all appear in the spectra.

FIG. 11 shows a photograph of the transmitter and receiver placed against a test sample cube of concrete (size 50×50×50 mm). Two concrete test samples were selected and are shown in this figure, one has a crack running through its entire length, the other is undamaged. The transmitter comprises a single piezoelectric wide band actuator that is continuously sending the sum of two sine waveforms at preprogrammed frequencies.

FIG. 28 shows the time and spectrum plots for the received waveform having passed through each of the concrete test cubes. The difference in the amplitude of the two frequencies results from the ultrasonic attenuation of concrete being frequency dependent, losses are greater at higher frequencies. The data for the damaged sample is shown in blue, and the good sample shown in red. The damaged sample shows clearly that harmonics and intermodulation products have been generated by the crack. The upper side band (f1+f2) at 160 KHz is below 0.5% for the good sample and rises above 1% in the damaged sample. The second harmonic of f2 at 240 kHz changes from, 56 dB (0.16%) in the good sample and rising above 0.5% in the damaged sample. The effect of the combinations of the harmonics and intermodulation products are very noticeable in the frequency range 200 to 350 kHz. For example, 2f2 (240 kHz), 2f1+f2 (200 kHz), f1+2f2 (280 kHz) and 2f1+2f2 (320 kHz). The result is the formation of peaks and troughs within this range, corresponding to the interaction of their frequencies and phases, this effect can mask the changes between the good and bad samples. The correct choice of the two frequencies f2 and f1 is an important factor. FIG. 29 illustrates this by showing the spectra resulting from two different frequency combinations, f1+f2 is reduced by the effect of the third harmonic of f1 (3*f1).

Figure 30:
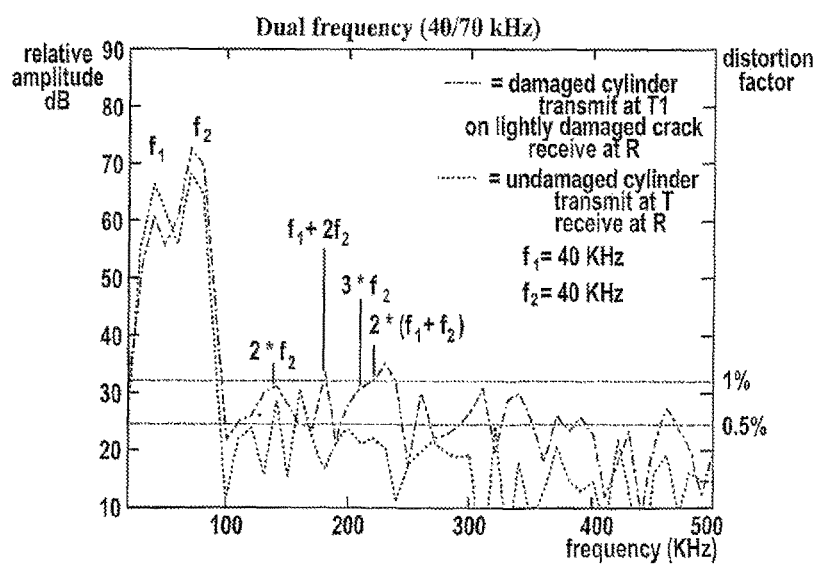

FIG. 30 shows a spectral plot taken over the surface of a mildly damaged region of the concrete test cylinders, shown previously in FIG. 21. This test was performed at the two frequencies 40 and 70 kHz. The two fundamental frequencies are not sufficiently separated to form clear spectral peaks, however the intermodulation products and in particular the second multiple of f1+f2 that is 2*(f1+f2) shows a very clear peak above 1% distortion in the damaged region.

FIG. 31 shows a dual frequency being applied to the microdamaged drilled core. The dual frequency ultrasonic waveform was transmitted through the sample at two locations, one along the crack, shown in blue and the other away from the crack shown in red. The difference between the two locations is very clear. The cracked region produces harmonics and intermodulation products well above 0.5% distortion factor and f1+f2 is above 1%. The less cracked region has all levels below 0.5% and for frequencies above 250 kHz is below 0.25%.

FIG. 32 shows the same core but this time tested on one side only, the receiver positions are indicated by the letter R and the transmitter positions by letter T. The red trace corresponds to a position away from the crack and the blue near to the crack. There is less difference between the two positions at low frequency however at higher frequencies, above 300 kHz, the cracked region does produce a significantly higher levels of intermodulation produces particularly at 3f2+f1(310 KHz).

As can be seen in FIG. 33, the transmitter 43 may be powered by a signal generator 46 and the receiver 44 may transmit its output to a monitor/comparator 47 which measures the amplitude of the harmonics and/or intermodulation products to compare them with one or more predetermine levels (e.g. the 0.5% and 1% levels previously indicated). The monitor comparator 47 may then produce either pass or fail signals or pass, check or fail signals which can be displayed by indicator 48 for example using a red and green light display or a red, amber, green display, as shown at 49.

The invention claimed is:

1. A method of detecting a defect in a workpiece including:
   inputting a first impulse at a location into a workpiece, and detecting a first resultant vibration in the workpiece to generate a first output signal,
   subsequently inputting a second impulse into said workpiece at the same location as said first impulse,
   the second impulse being of equal amplitude to said first impulse but
   180° out of phase with said first impulse, and
   detecting a second resultant vibration to generate a second output signal; the method further comprising monitoring the amplitudes of the first and second output signals for determining the presence or absence of a defect.

2. A method as claimed in claim 1 wherein the impulses are ultrasonic impulses.

3. A method as claimed in claim 2 wherein the respective maximum amplitudes of the output signals are compared by forming a ratio, the value of which is indicative of the presence or absence of a defect.

4. A method as claimed in claim 2 wherein the output signals are summed and the amplitude of the summed signals is monitored to determine the presence or absence of a defect.

5. A method as claimed in claim 2 wherein the transition of the waveform is monitored to determine the presence or absence of a defect.

6. A method as claimed in claim 1 wherein the step of inputting two impulses includes providing at least one transmitter in contact with the workpiece.

7. A method as claimed in claim 1 wherein the step of detecting the resultant vibrations includes providing at least one receiver in contact with the workpiece.

8. A device for use in detecting a defect in a workpiece including: (a) a broadband transducer for contacting the workpiece;
(b) a driving circuit connectable to the transducer to operate the transducer in an actuator mode;
(c) a signal output circuit connectable to operate the transducer in a sensor mode; and
(d) a control for selectively connecting the transducer to the driving circuit or the signal output circuit,
wherein the driving circuit includes at least a pair of oscillators for generating signals of at least frequencies F1 and F2 respectively and a summer for summing the signals F1, F2 to provide a driving signal for the transducer and wherein the signals F1 and F2 interact within said workpiece and will be subject to intermodulation in the presence of a non-linearity in the workpiece.

9. A device as claimed in claim 8 further including a data interface.

10. A device as claimed in claim 9 wherein a microprocessor forms both the control and the interface.

11. A device as claimed in claim 10 wherein the microprocessor is linked to at least one of an analogue-to-digital convertor; a digital-to-analogue convertor; data memory; a wireless connection and communication link.

12. A device as claimed in claim 11 wherein the memory is addressable either by the microprocessor or an external clock counter.

13. A defect detecting system including an array of devices, as claimed in claim 8, and a central computer or other electronics linked to the interface of each device by a communication link.

14. A system as claimed in claim 13 wherein the computer is arranged for generating control signals to be sent by the communication link to instruct the controls of the respective devices to operate the associated transducer in an actuator or sensor mode.

15. A system as claimed in claim 13 wherein the devices are embedded in a workpiece.

16. A system as claimed in claim 13 including a dedicated sensor.

17. A system as claimed in claim 13 wherein the system includes a monitor for monitoring the signal received by at least one device, in sensor mode, and for protecting harmonics or intermodulation products in the sensor output signal and producing an output in response to that detection.

* * * * *